(12) United States Patent
Tegels

(10) Patent No.: US 9,107,646 B2
(45) Date of Patent: Aug. 18, 2015

(54) ACTIVE SECUREMENT DETACHABLE SEALING TIP FOR EXTRA-VASCULAR CLOSURE DEVICE AND METHODS

(71) Applicant: St. Jude Medical Puerto Rico LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 278 days.

(21) Appl. No.: 13/794,581

(22) Filed: Mar. 11, 2013

(65) Prior Publication Data

US 2014/0257375 A1    Sep. 11, 2014

(51) Int. Cl.
*A61B 17/03*    (2006.01)
*A61B 17/00*    (2006.01)

(52) U.S. Cl.
CPC ................................. *A61B 17/0057* (2013.01)

(58) Field of Classification Search
CPC .............. A61B 17/0057; A61B 2017/00637; A61B 2017/00646; A61B 2017/0065; A61B 2017/00654; A61B 2017/00659; A61B 2017/00778
See application file for complete search history.

(56) References Cited

U.S. PATENT DOCUMENTS

| | | | | | |
|---|---|---|---|---|---|
| 5,292,332 | A | * | 3/1994 | Lee | 606/213 |
| 5,690,674 | A | * | 11/1997 | Diaz | 606/213 |
| 5,906,631 | A | * | 5/1999 | Imran | 606/213 |
| 6,056,768 | A | * | 5/2000 | Cates et al. | 606/213 |
| 6,063,114 | A | * | 5/2000 | Nash et al. | 623/1.36 |
| 6,162,240 | A | * | 12/2000 | Cates et al. | 606/213 |
| 6,183,496 | B1 | * | 2/2001 | Urbanski | 606/213 |
| 6,334,865 | B1 | * | 1/2002 | Redmond et al. | 606/213 |
| 6,350,280 | B1 | * | 2/2002 | Nash et al. | 623/1.36 |
| 6,371,975 | B2 | * | 4/2002 | Cruise et al. | 606/214 |
| 6,458,147 | B1 | * | 10/2002 | Cruise et al. | 606/214 |
| 6,508,828 | B1 | * | 1/2003 | Akerfeldt et al. | 606/215 |
| 6,613,070 | B2 | * | 9/2003 | Redmond et al. | 606/213 |
| 6,699,262 | B2 | * | 3/2004 | Redmond et al. | 606/213 |
| 6,830,756 | B2 | * | 12/2004 | Hnojewyj | 424/426 |
| 6,860,895 | B1 | * | 3/2005 | Akerfeldt et al. | 606/215 |
| 6,863,680 | B2 | * | 3/2005 | Ashby | 606/213 |
| 6,890,342 | B2 | * | 5/2005 | Zhu et al. | 606/213 |
| 6,923,820 | B1 | * | 8/2005 | Nash et al. | 606/153 |
| 6,994,686 | B2 | * | 2/2006 | Cruise et al. | 604/82 |

(Continued)

FOREIGN PATENT DOCUMENTS

WO    2010118312 A2    10/2010
WO    2012148745 A1    11/2012

OTHER PUBLICATIONS

PCT International Search Report for International Application No. PCT/US2014/019855, mailed Jun. 23, 2014 (2 pp.).

*Primary Examiner* — Ryan Severson
(74) *Attorney, Agent, or Firm* — Holland & Hart

(57) ABSTRACT

A vascular closure device includes a carrier tube, a sealing tip, and a sealing tip connection member. The carrier tube includes a distal end. The sealing tip is releasably connected to the distal end of the carrier tube. The sealing tip connection member extends through the sealing tip and includes a proximal portion extending proximally from the sealing tip. Applying a tension force at the proximal portion of the sealing tip connection member removes the sealing tip connection member from the sealing tip, and removing the sealing tip connection member from the sealing tip radially expands a portion of the sealing tip.

24 Claims, 15 Drawing Sheets

(56) References Cited

U.S. PATENT DOCUMENTS

| | | | |
|---|---|---|---|
| 7,060,084 B1* | 6/2006 | Loshakove et al. | 606/213 |
| 7,264,624 B2* | 9/2007 | Nash et al. | 606/153 |
| 7,316,704 B2* | 1/2008 | Bagaoisan et al. | 606/213 |
| 7,318,933 B2* | 1/2008 | Hnojewyj | 424/426 |
| 7,331,979 B2* | 2/2008 | Khosravi et al. | 606/213 |
| 7,553,319 B2* | 6/2009 | Bagaoisan et al. | 606/214 |
| 7,695,483 B2* | 4/2010 | Nash et al. | 606/153 |
| 7,780,699 B2* | 8/2010 | Zhu et al. | 606/213 |
| 7,942,301 B2* | 5/2011 | Sater | 227/175.1 |
| 7,985,240 B2* | 7/2011 | Bagaoisan et al. | 606/213 |
| 8,012,167 B2* | 9/2011 | Zhu et al. | 606/213 |
| 8,034,367 B2* | 10/2011 | Hnojewyj | 424/426 |
| 8,083,768 B2* | 12/2011 | Ginn et al. | 606/232 |
| 8,088,145 B2* | 1/2012 | Zhu et al. | 606/213 |
| 8,128,654 B2* | 3/2012 | Khosravi et al. | 606/213 |
| 8,262,693 B2* | 9/2012 | Pai et al. | 606/213 |
| 8,303,624 B2* | 11/2012 | Fortson | 606/213 |
| 8,317,822 B2* | 11/2012 | Wicks et al. | 606/213 |
| 8,337,522 B2* | 12/2012 | Ditter | 606/213 |
| 8,377,080 B2* | 2/2013 | Nash et al. | 606/153 |
| 8,383,144 B2* | 2/2013 | Hnojewyj | 424/426 |
| 8,398,677 B2* | 3/2013 | Lafontaine et al. | 606/213 |
| 8,425,552 B2* | 4/2013 | Zhu et al. | 606/213 |
| 8,491,628 B2* | 7/2013 | Zhu et al. | 606/213 |
| 8,506,592 B2* | 8/2013 | Killion et al. | 606/213 |
| 8,617,253 B2* | 12/2013 | Zhu et al. | 623/23.72 |
| 8,702,750 B2* | 4/2014 | Zhu et al. | 606/213 |
| 8,753,362 B2* | 6/2014 | Widomski et al. | 606/151 |
| 8,758,398 B2* | 6/2014 | Carley | 606/213 |
| 8,758,400 B2* | 6/2014 | Ginn et al. | 606/213 |
| 8,801,744 B2* | 8/2014 | McCrystle et al. | 606/198 |
| 8,840,640 B2* | 9/2014 | Pipenhagen et al. | 606/213 |
| 8,845,683 B2* | 9/2014 | Killion et al. | 606/213 |
| 8,852,229 B2* | 10/2014 | Ginn | 606/213 |
| 8,945,178 B2* | 2/2015 | Pai et al. | 606/213 |
| 2001/0018598 A1* | 8/2001 | Cruise et al. | 606/214 |
| 2001/0031948 A1* | 10/2001 | Cruise et al. | 604/191 |
| 2001/0051813 A1* | 12/2001 | Hnojewyj | 606/213 |
| 2002/0006429 A1* | 1/2002 | Redmond et al. | 424/425 |
| 2002/0026215 A1* | 2/2002 | Redmond et al. | 606/213 |
| 2002/0032463 A1* | 3/2002 | Cruise et al. | 606/214 |
| 2002/0072767 A1* | 6/2002 | Zhu | 606/213 |
| 2002/0161399 A1* | 10/2002 | Cruise et al. | 606/214 |
| 2003/0032981 A1* | 2/2003 | Kanner et al. | 606/219 |
| 2003/0088269 A1* | 5/2003 | Ashby | 606/213 |
| 2003/0109866 A1* | 6/2003 | Edwards et al. | 606/41 |
| 2004/0054346 A1* | 3/2004 | Zhu et al. | 604/507 |
| 2004/0093027 A1* | 5/2004 | Fabisiak et al. | 606/215 |
| 2004/0122349 A1* | 6/2004 | Lafontaine et al. | 604/11 |
| 2004/0162578 A1* | 8/2004 | Redmond et al. | 606/213 |
| 2004/0249342 A1* | 12/2004 | Khosravi et al. | 604/96.01 |
| 2004/0267193 A1* | 12/2004 | Bagaoisan et al. | 604/82 |
| 2004/0267307 A1* | 12/2004 | Bagaoisan et al. | 606/213 |
| 2004/0267308 A1* | 12/2004 | Bagaoisan et al. | 606/213 |
| 2005/0085852 A1* | 4/2005 | Ditter | 606/213 |
| 2005/0085854 A1* | 4/2005 | Ginn | 606/213 |
| 2005/0085858 A1* | 4/2005 | Hnojewyj | 606/214 |
| 2005/0107826 A1* | 5/2005 | Zhu et al. | 606/213 |
| 2005/0149117 A1* | 7/2005 | Khosravi et al. | 606/215 |
| 2005/0209637 A1* | 9/2005 | Zhu et al. | 606/213 |
| 2005/0245946 A1* | 11/2005 | Nash et al. | 606/153 |
| 2005/0267528 A1* | 12/2005 | Ginn et al. | 606/214 |
| 2005/0273119 A1* | 12/2005 | Widomski et al. | 606/151 |
| 2005/0283188 A1* | 12/2005 | Loshakove et al. | 606/213 |
| 2006/0058844 A1* | 3/2006 | White et al. | 606/232 |
| 2006/0088570 A1* | 4/2006 | Cruise et al. | 424/423 |
| 2006/0100664 A1* | 5/2006 | Pai et al. | 606/214 |
| 2006/0116635 A1* | 6/2006 | Van Heugten et al. | 604/103.01 |
| 2006/0167482 A1* | 7/2006 | Swain et al. | 606/151 |
| 2006/0173492 A1* | 8/2006 | Akerfeldt et al. | 606/232 |
| 2006/0287674 A1* | 12/2006 | Ginn et al. | 606/221 |
| 2007/0123816 A1* | 5/2007 | Zhu et al. | 604/57 |
| 2007/0149998 A1* | 6/2007 | Wicks et al. | 606/213 |
| 2007/0149999 A1* | 6/2007 | Szabo et al. | 606/214 |
| 2007/0293881 A1* | 12/2007 | Nash et al. | 606/153 |
| 2008/0004569 A1* | 1/2008 | McCrystle et al. | 604/104 |
| 2008/0058862 A1* | 3/2008 | Khosravi et al. | 606/213 |
| 2008/0058864 A1* | 3/2008 | Bagaoisan et al. | 606/214 |
| 2008/0065152 A1* | 3/2008 | Carley | 606/215 |
| 2008/0108577 A1* | 5/2008 | Hnojewyj | 514/21 |
| 2008/0287988 A1* | 11/2008 | Smith et al. | 606/216 |
| 2008/0312683 A1* | 12/2008 | Drasler et al. | 606/213 |
| 2009/0082802 A1* | 3/2009 | Benjamin et al. | 606/213 |
| 2009/0171387 A1* | 7/2009 | Pipenhagen et al. | 606/213 |
| 2009/0228040 A1* | 9/2009 | Mas et al. | 606/216 |
| 2009/0259249 A1* | 10/2009 | Lobello | 606/219 |
| 2009/0264923 A1* | 10/2009 | Sater | 606/219 |
| 2010/0087854 A1* | 4/2010 | Stopek et al. | 606/215 |
| 2010/0168007 A1* | 7/2010 | Cruise et al. | 514/12 |
| 2010/0168767 A1* | 7/2010 | Yassinzadeh et al. | 606/139 |
| 2010/0173843 A1* | 7/2010 | Hnojewyj | 514/12 |
| 2010/0179567 A1* | 7/2010 | Voss et al. | 606/139 |
| 2010/0179590 A1* | 7/2010 | Fortson et al. | 606/216 |
| 2010/0211000 A1* | 8/2010 | Killion et al. | 604/57 |
| 2010/0217290 A1* | 8/2010 | Nash et al. | 606/153 |
| 2010/0234884 A1* | 9/2010 | Lafontaine et al. | 606/213 |
| 2011/0046664 A1* | 2/2011 | Zhu et al. | 606/213 |
| 2011/0106148 A1* | 5/2011 | Ginn et al. | 606/213 |
| 2011/0224719 A1* | 9/2011 | Fortson | 606/213 |
| 2011/0282383 A1* | 11/2011 | Vidlund et al. | 606/213 |
| 2011/0288563 A1* | 11/2011 | Gianotti et al. | 606/144 |
| 2012/0059410 A1* | 3/2012 | Zhu et al. | 606/213 |
| 2012/0101520 A1* | 4/2012 | Ginn et al. | 606/213 |
| 2012/0143246 A1* | 6/2012 | Zhu et al. | 606/215 |
| 2012/0296372 A1* | 11/2012 | Ziobro | 606/213 |
| 2013/0066361 A1* | 3/2013 | Pai et al. | 606/213 |
| 2013/0103077 A1* | 4/2013 | Ditter | 606/213 |
| 2013/0190808 A1* | 7/2013 | Tegels et al. | 606/213 |
| 2013/0190812 A1* | 7/2013 | Vidlund | 606/214 |
| 2013/0218203 A1* | 8/2013 | Zhu et al. | 606/213 |
| 2013/0231701 A1* | 9/2013 | Voss et al. | 606/232 |
| 2013/0281785 A1* | 10/2013 | Zhu et al. | 600/205 |
| 2013/0338707 A1* | 12/2013 | Killion et al. | 606/213 |
| 2014/0025095 A1* | 1/2014 | Widomski et al. | 606/151 |
| 2014/0058443 A1* | 2/2014 | Zhu et al. | 606/215 |
| 2014/0114349 A1* | 4/2014 | Tegels | 606/213 |
| 2014/0180335 A1* | 6/2014 | Zhu et al. | 606/213 |
| 2014/0222066 A1* | 8/2014 | Tegels | 606/213 |
| 2014/0236186 A1* | 8/2014 | Smith et al. | 606/142 |
| 2014/0309686 A1* | 10/2014 | Ginn et al. | 606/216 |

* cited by examiner

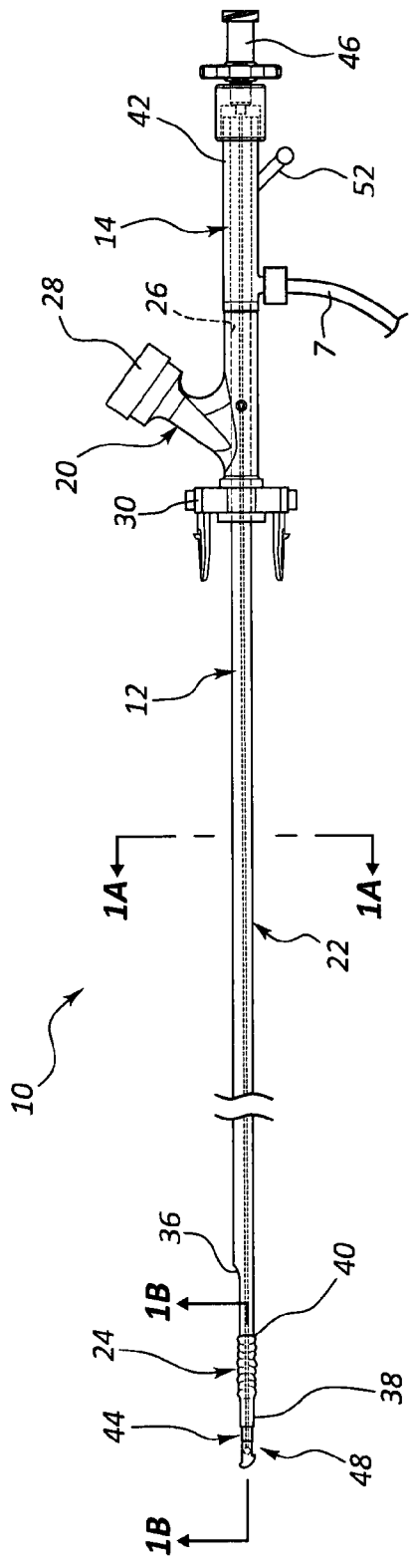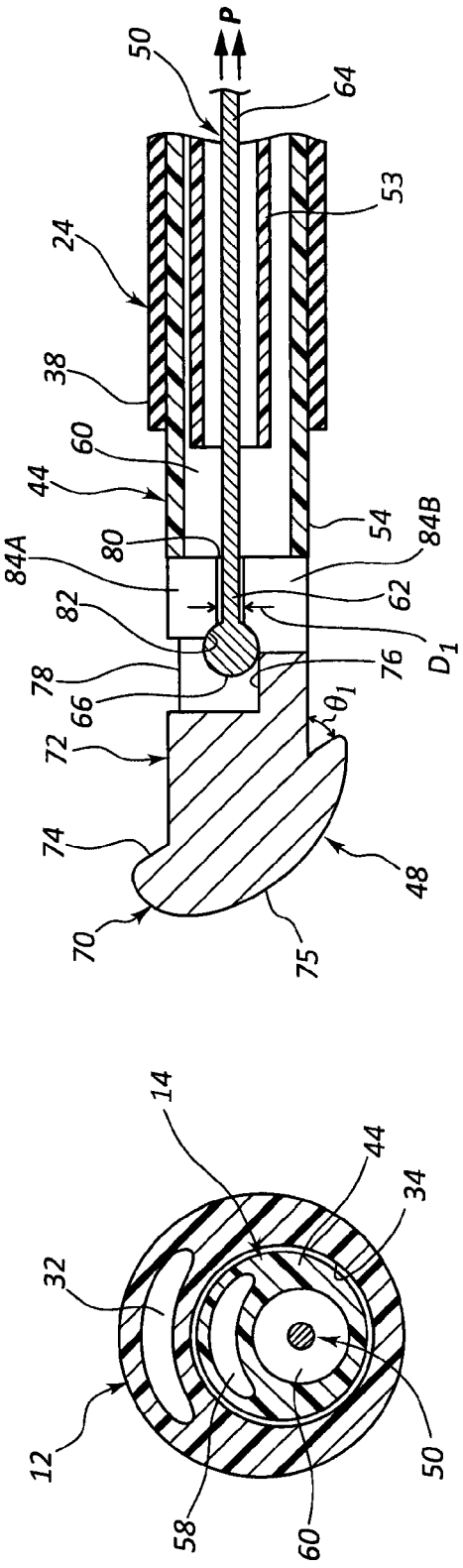
FIG. 1
FIG. 1A
FIG. 1B

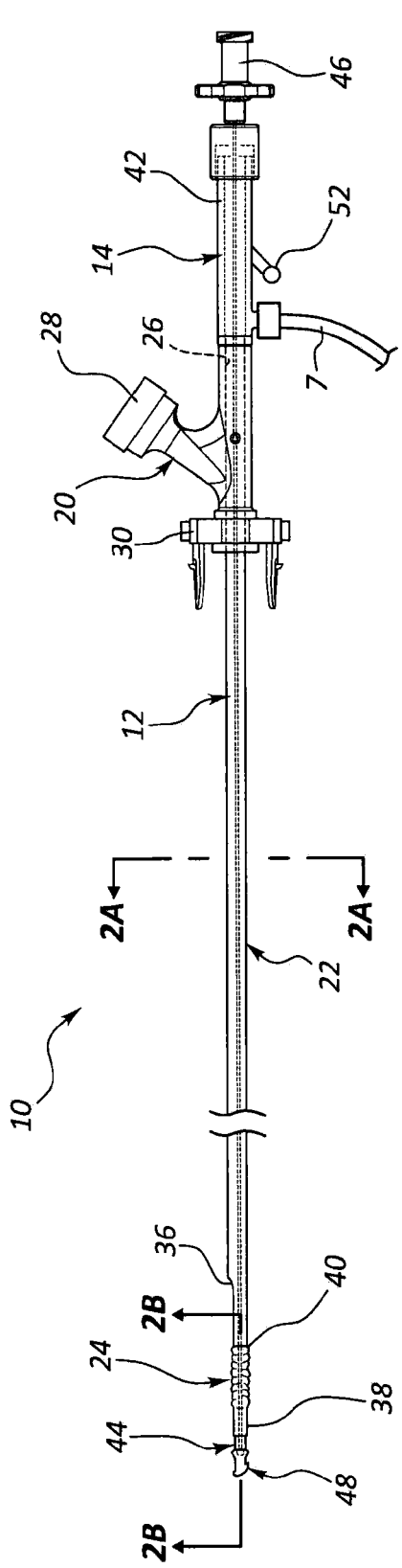
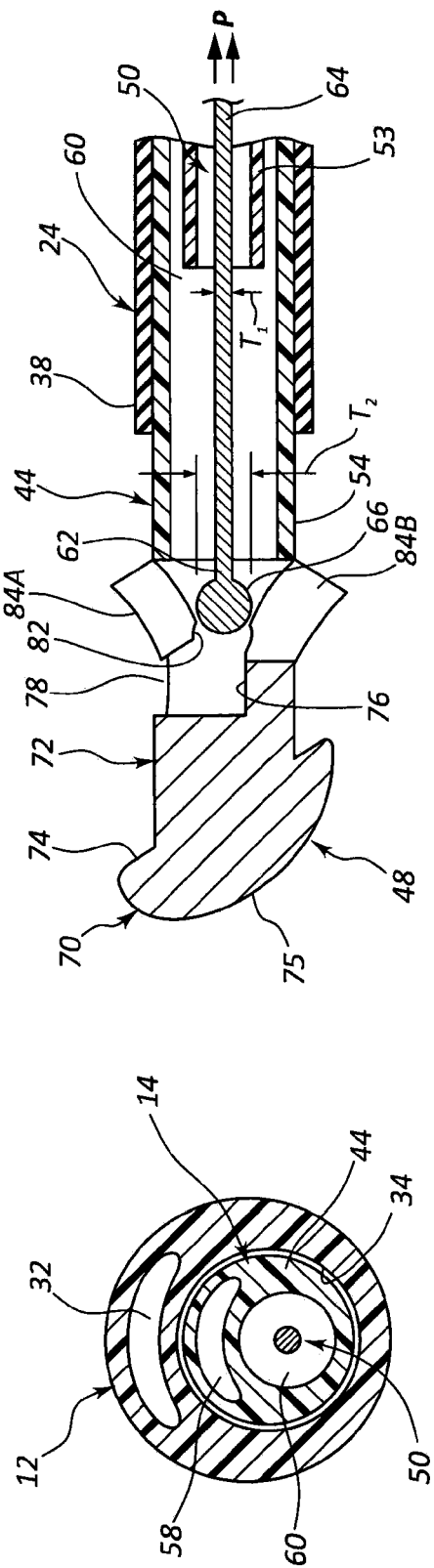
FIG. 2
FIG. 2A
FIG. 2B

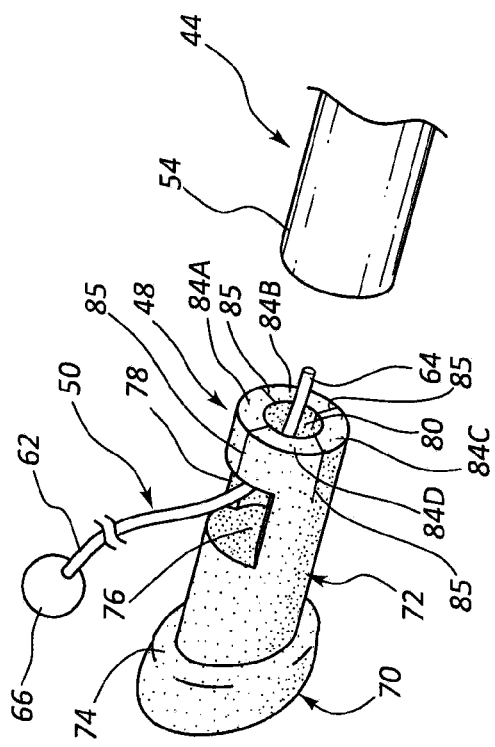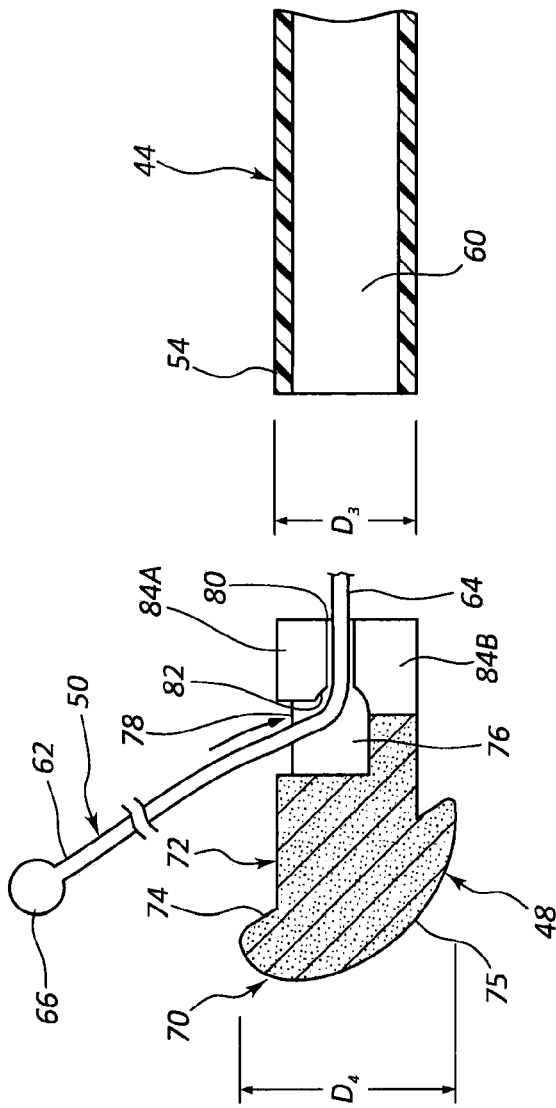

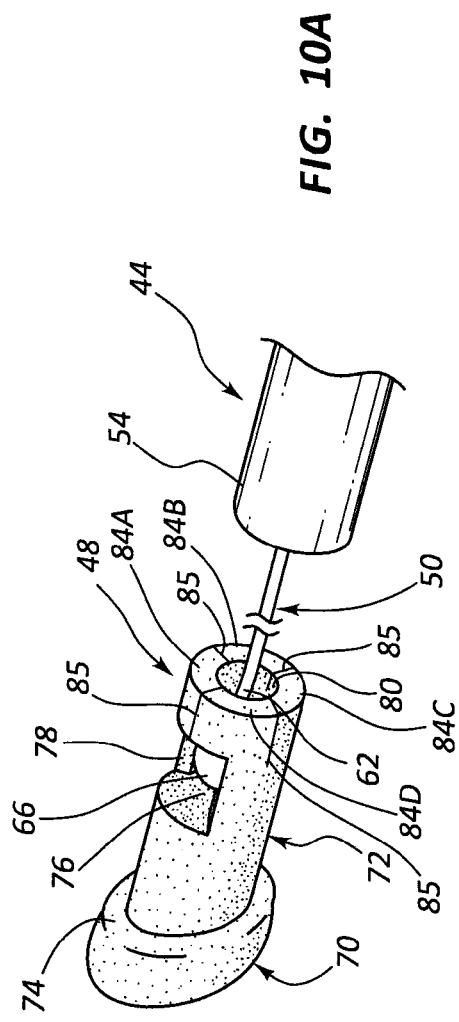
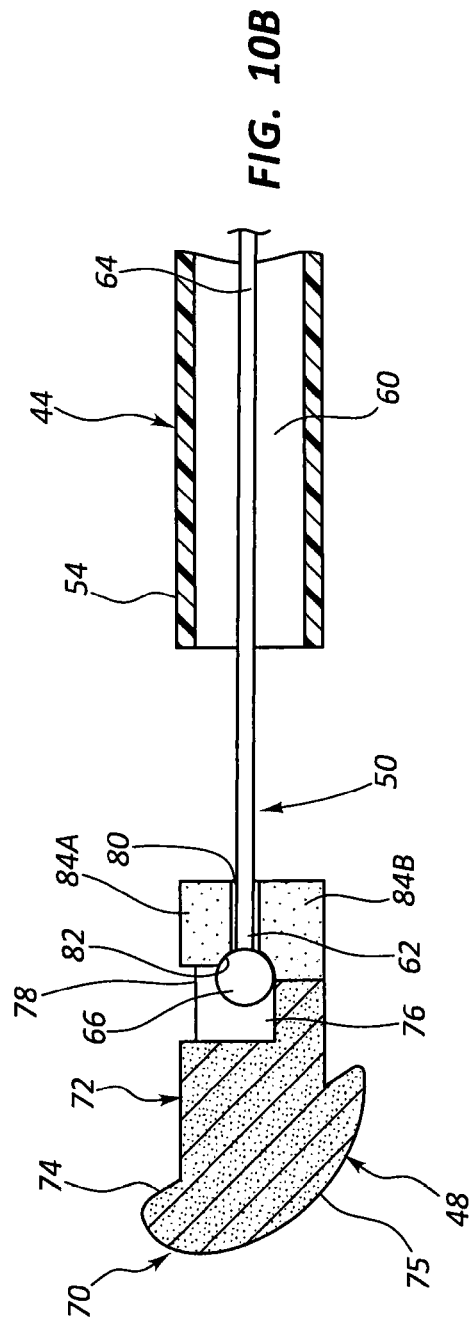
FIG. 10A
FIG. 10B

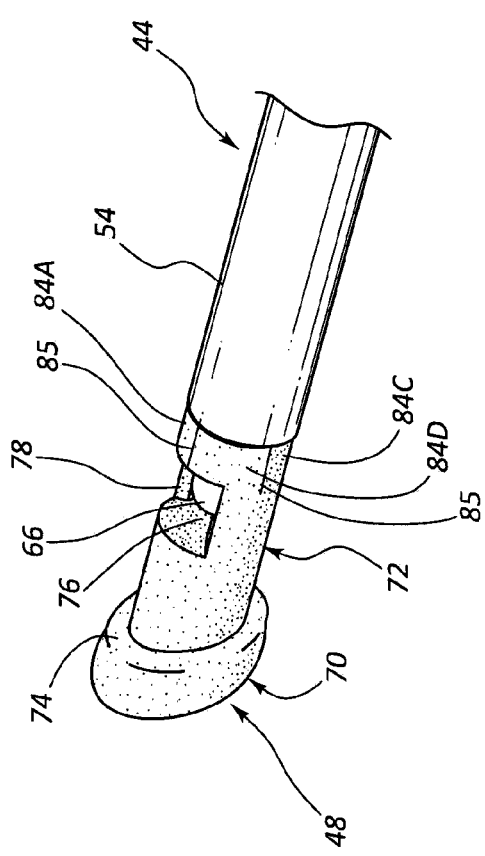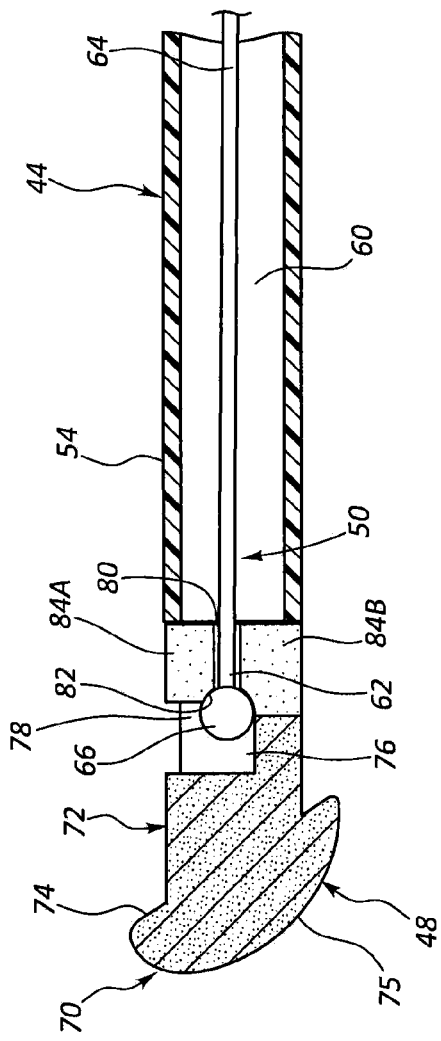

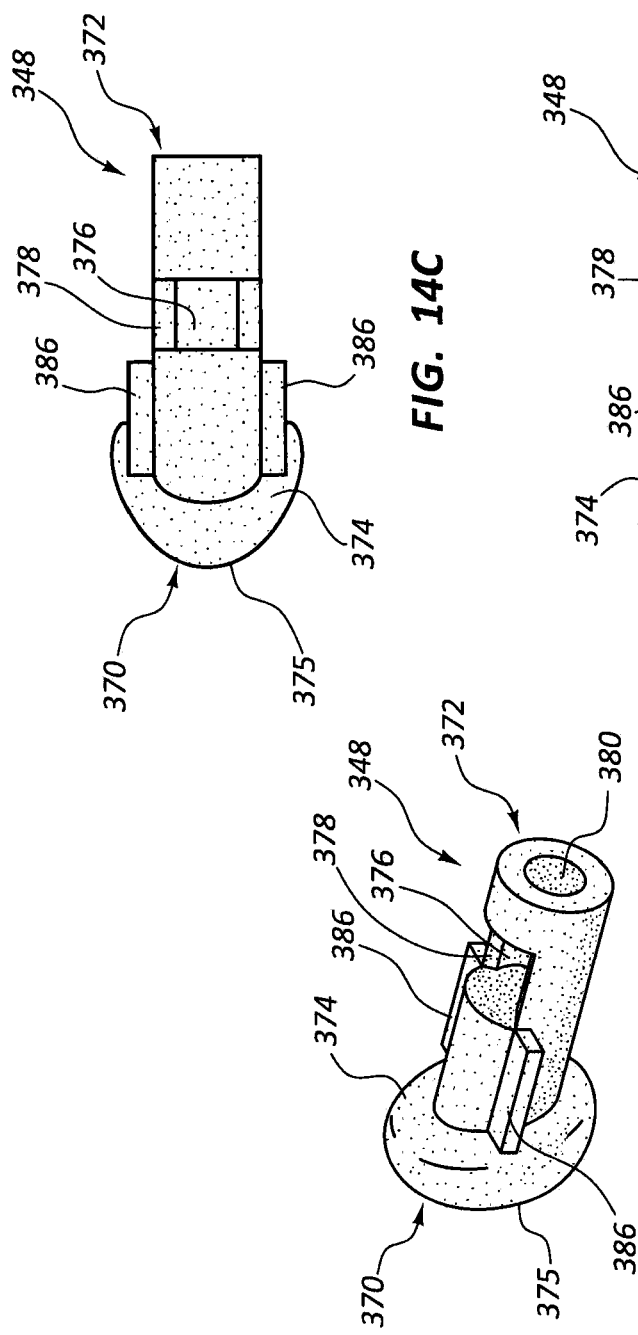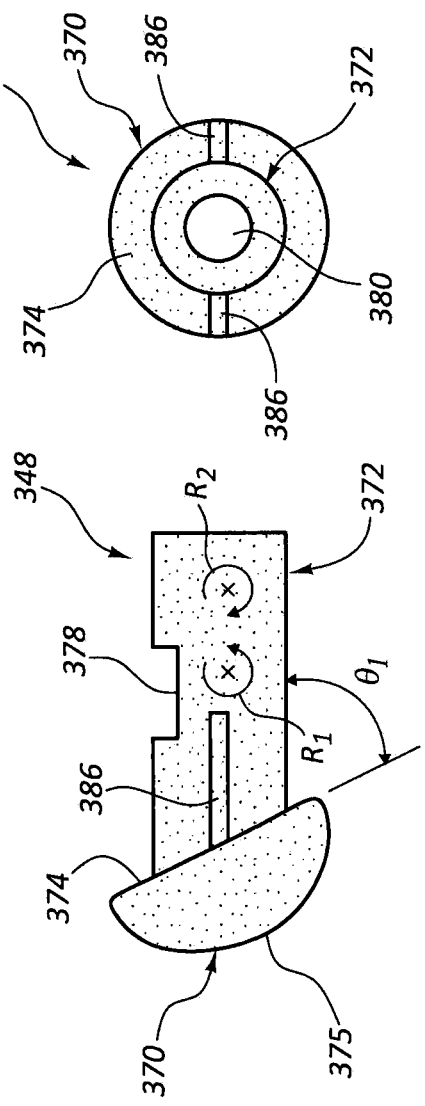

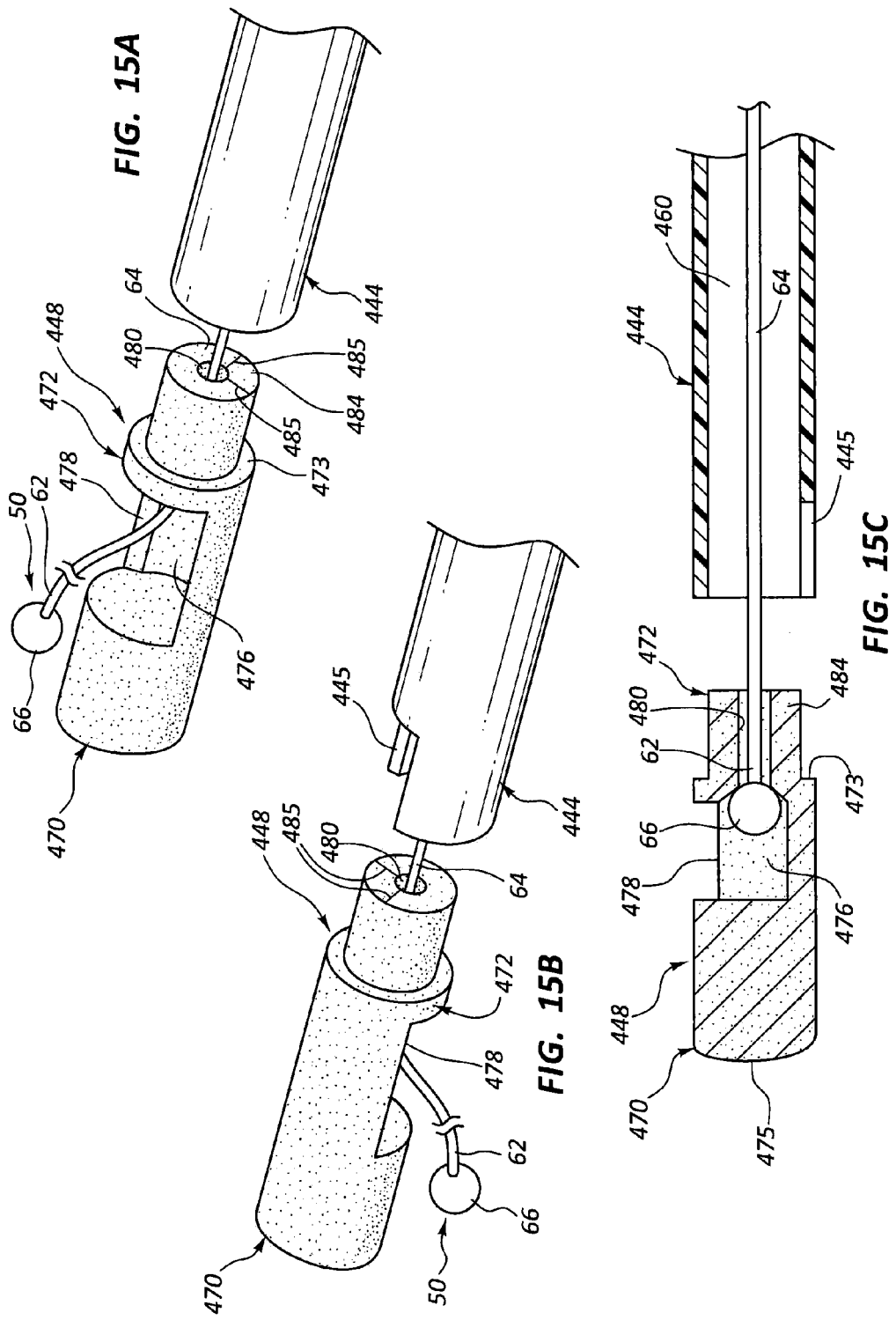

ACTIVE SECUREMENT DETACHABLE SEALING TIP FOR EXTRA-VASCULAR CLOSURE DEVICE AND METHODS

TECHNICAL FIELD

The present disclosure relates generally to methods and systems for sealing tissue punctures, and more particularly, to methods and systems for depositing a sealing member to seal tissue punctures.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one method includes temporarily sealing the vessel puncture intravascularly using an inflation balloon. A sealant may be delivered to an outer surface of the vessel to seal the vessel puncture while the temporary seal from the balloon is maintained. Removing the collapsed balloon through the sealant may leave a tract or channel through the sealant. Challenges exist in closing the tract to maintain hemostasis.

SUMMARY

One aspect of the present disclosure relates to a vascular closure device that includes a carrier tube, a sealing tip, and a sealing tip connection member. The carrier tube includes a distal end. The sealing tip is releasably connected to the distal end of the carrier tube. The sealing tip connection member extends through the sealing tip and includes a proximal portion extending proximally from the sealing tip. Applying a tension force at the proximal portion of the sealing tip connection member removes the sealing tip connection member from the sealing tip, and removing the sealing tip connection member from the sealing tip radially expands a portion of the sealing tip.

The sealing tip connection member may include a wire having a retention member at a distal end thereof, and applying a tension force in the wire may pull the retention member through the sealing tip. The sealing tip may include a body portion and a head portion, wherein the body portion may include a proximal passage through which the sealing tip connection member passes. The head portion may include a distal end surface arranged at a non-perpendicular angle relative to a longitudinal dimension of the body portion. The carrier tube may include a lumen, and the sealing tip connection member may extend through the lumen. The vascular closure device may include a hypotube extending through the lumen, and the sealing tip connection member may extend through the hypotube.

The sealing tip may include a cavity sized to receive a retention member of the sealing tip connection member, wherein the retention member may exert a radially outward directed force to the sealing tip as the sealing tip connection member is removed from the sealing tip. The cavity may be accessible from a first opening in a sidewall of the sealing tip and a second opening in a distal end portion of the sealing tip, wherein the sealing tip connection member may be insertable through the first opening and out of the second opening with the retention member being retained in the cavity. The sealing tip may include a plurality of radially expandable arms positioned at a proximal end of the sealing tip. The plurality of radially expandable arms may be arranged circumferentially about a proximal passage of the sealing tip, and removing the sealing tip connection member from the sealing tip may include passing the sealing tip connection member through the proximal passage to radially expand the plurality of radially expandable arms.

Another aspect of the present disclosure relates to a vascular closure device for sealing a vessel puncture of a patient. The vascular closure device includes a sealant delivery device and a detachable sealing tip assembly. The sealant delivery device is configured to deposit a volume of flowable sealant adjacent to a vessel puncture. The detachable sealing tip assembly is configured to seal a channel formed in the volume of flowable sealant upon removal of the vascular closure device from the patient. The detachable sealing tip assembly includes a carrier tube, a sealing tip positioned at a distal end of the carrier tube, and a filament having a proximal end and a distal end releasably connected to the sealing tip. Applying a tension force at the proximal end radially expands a portion of the sealing tip to lodge the sealing tip within the channel.

The sealant delivery device may include a lumen sized to receive the carrier tube. The sealing tip may include a proximal portion having a plurality of expandable arms that expand radially upon disconnecting the filament from the sealing tip. The filament may include a connection portion at the distal end, wherein the connection portion may be positioned within the sealing tip, and disconnecting the filament from the sealing tip radially expands a portion of the sealing tip. The sealing tip may include a head portion at the distal end, wherein the head portion having a tapered construction.

Another aspect of the present disclosure relates to a method of sealing a vessel puncture. The method includes providing a vascular closure device having a carrier tube, a sealing tip releasably mounted to the carrier tube, and a sealing tip connection member extending proximally from the sealing tip. The method also includes advancing the vascular closure device to the vessel puncture, delivering a volume of flowable sealant to the vessel puncture, withdrawing a portion of the vascular closure device through the volume of flowable sealant to form a channel in the volume of flowable sealant, positioning the sealing tip in the channel, expanding the sealing tip with the sealing tip connection member, and disconnecting the sealing tip connection member from the sealing tip to deposit the sealing tip in the channel.

Disconnecting the sealing tip connection member from the sealing tip may include removing a connection portion of the sealing tip connection member from within the sealing tip. Removing the connection portion from within the sealing tip may radially expand a portion of the sealing tip. Disconnecting the sealing tip connection member from the sealing tip may disconnect the sealing tip from the carrier tube. The sealing tip may include at least one radially expandable arm, and expanding the sealing tip may include moving the at least one radially expandable arm into an expanded position. The method may include providing a sealant delivery device to deliver the volume of flowable sealant to the vessel puncture, wherein the vascular closure device extends through the sealant delivery device.

Another example method in accordance with the present disclosure relates to a method of sealing a vessel puncture. The method includes providing a vascular closure device having a sealing tip and a sealing tip connection member, wherein the sealing tip connection member extends through a portion of the sealing tip. The method further includes advancing the vascular closure device to the vessel puncture, depositing a flowable sealant adjacent to the vessel puncture, withdrawing a portion of the vascular closure device through the deposited flowable sealant to form a channel therein, positioning the sealing tip in the channel, disconnecting the sealing tip connection member from the sealing tip to deposit the sealing tip in the channel, and rotating the sealing tip within the channel to fix an axial position of the sealing tip in the channel.

Rotating the sealing tip may include rotating about an axis arranged perpendicular to a length dimension of the sealing tip. The sealing tip may include a head portion, a body portion, and a step feature defined between the head portion and the body portion, and the method may include contacting the step feature with a surface of the channel when the sealing tip rotates within the channel.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example vascular closure device in accordance with the present disclosure.

FIG. 1A is a cross-sectional view of the vascular closure device of FIG. 1 taken along cross-section indicators 1A-1A.

FIG. 1B is a cross-sectional view of the vascular closure device of FIG. 1 taken along cross-section indicators 1B-1B.

FIG. 2 is a side view of the vascular closure device of FIG. 1 being operated to release a sealing tip.

FIG. 2A is a cross-sectional view of the vascular closure device of FIG. 2 taken along cross-section indicators 2A-2A.

FIG. 2B is a cross-sectional view of the vascular closure device of FIG. 2 taken along cross-section indicators 2B-2B.

FIG. 9A is an exploded perspective view of a portion of the vascular closure device of FIG. 1 in a first state of assembly.

FIG. 9B is a cross-sectional view of the vascular closure device of FIG. 9A.

FIG. 10A is an exploded perspective view of the vascular closure device of FIG. 1 in a second stage of assembly.

FIG. 10B is a cross-sectional view of the vascular closure device of FIG. 10A.

FIG. 11A is a perspective view of a portion of the vascular closure device of FIG. 1 in a third stage of assembly.

FIG. 11B is a cross-sectional view of the vascular closure device of FIG. 11A.

FIGS. 14A-14D show another example detachable sealing tip for use in the vascular closure devices disclosed herein.

FIG. 15A-15F show another example detachable sealing tip for use in the vascular closure devices disclosed herein.

Throughout the drawings, identical reference numbers designate similar, but not necessarily identical, elements.

DETAILED DESCRIPTION

Figure 3:
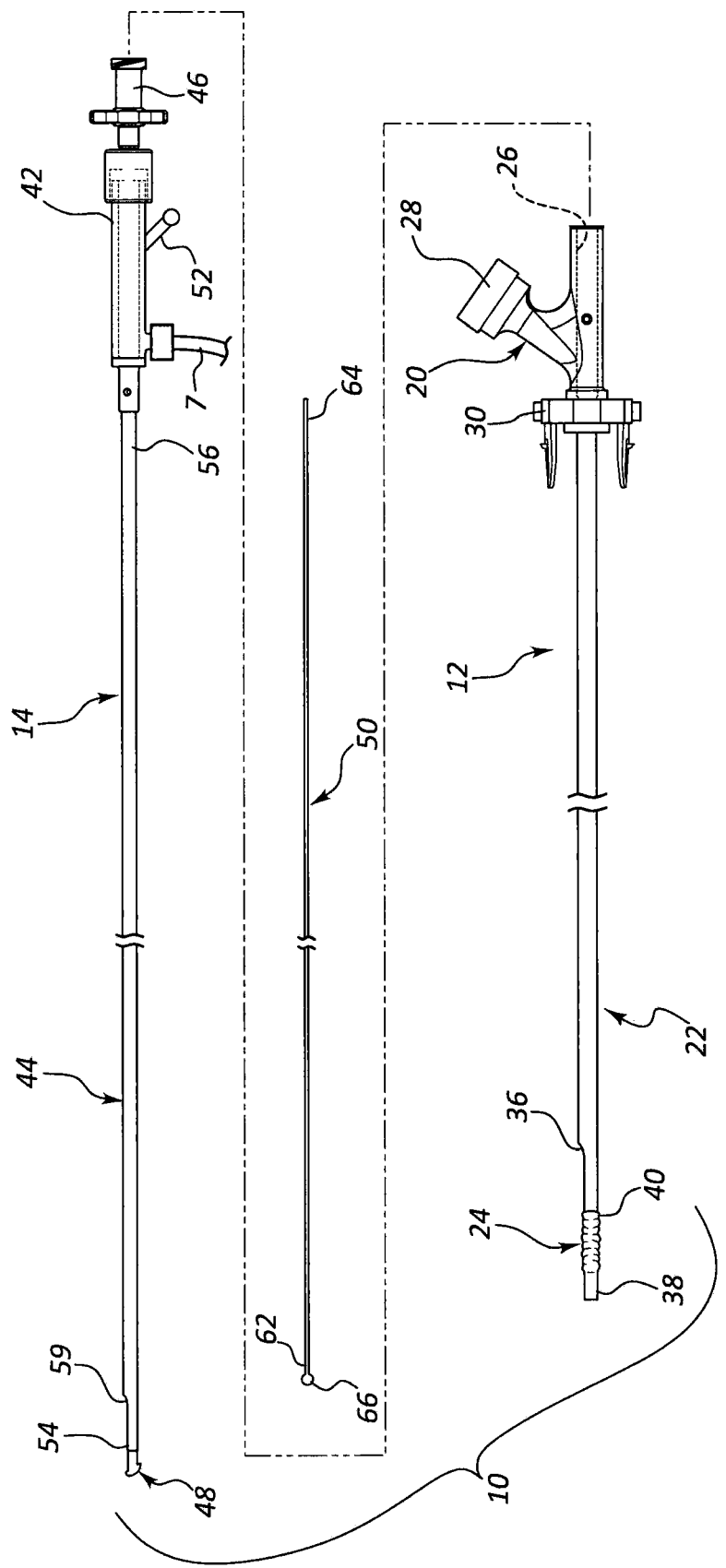
FIG. 3 is an exploded view of the vascular closure device of FIG. 1.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the terms "engage" and "engageable" are used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

An exemplary embodiment of the present disclosure includes a vascular closure device having a detachable sealing tip. The vascular closure device is used with a sheath that provides access through a vessel puncture and into an inner lumen of the vessel. The vascular closure device operates to release a detachable sealing plug (e.g., sealing tip) from a distal end of the vascular closure device after deployment of a flowable sealant at the vessel puncture. The vascular closure device may include a sealant delivery device and a locating device (also referred to as a temporary sealing device) such as a balloon location device. The locating device is inserted through the vessel puncture and anchors against an internal surface of the vessel adjacent to the vessel puncture. The vessel locating device may provide temporary hemostasis of the vessel puncture. The sealant delivery device deposits a volume of flowable sealant with the vessel puncture and along an external surface of the vessel adjacent to the vessel puncture. After the sealant is deposited and at least partially cured, the location device is withdrawn through the sealant, which leaves a channel through the sealant. The channel may be sealed by locating and releasing the sealing tip, which may be positioned at the distal end of the vascular closure device for depositing within the channel.

The sealing tip may be releasably connected at the distal end of the location device using an elongated connection member such as, for example, a wire, suture or other filament, which extends along a length of the location device from the sealing tip at a distal end of a location device to a proximal end of a location device for actuation by an operator. The connection member may be pulled proximally to release the sealing tip. The connection member may be cut at the distal or proximal end of the location device to release the detachable sealing tip. In another example, a wire having a connection portion at a distal end thereof is connected to the sealing tip with a snap-fit or press-fit connection. Applying a proximally directed tension force in the wire releases the connection so that the sealing tip may be deposited in the channel of the sealant.

The connection member (e.g., wire, suture or other filament), which secures the sealing plug (e.g., detachable sealing tip) to the location device, may extend through an inflation lumen of the location device. In other examples, the connection member may extend through a tube or lumen that extends along a length of the location device from the housing to the distal tip. In other examples, a separate lumen is provided in the location device through which the connection member extends. The separate lumen may be radially spaced apart from an inflation lumen, which is used to deliver inflation fluid to an expandable anchor member (e.g., inflatable balloon).

In other arrangements, the sealant delivery device includes multiple lumens, wherein one lumen provides delivery of sealant to the vessel puncture and the other lumen provides a passage for advancing the location device to the vessel puncture. The lumen that receives the location device may provide delivery of inflation fluid to a balloon or other locating device, which is positioned at a distal end portion of the location device or the sealant delivery device.

One aspect of the present disclosure relates to releasing the sealing tip within a channel of the deposited sealant without using the distal end of the delivery sheath or other device as a backstop to help locate and release the sealing tip. The step surface in the sealing tip in prior designs may define a catch point that inhibits precise placement of the sealing tip within the channel in the deposited sealant. The step surface in prior designs may also catch in a side branch vessel or plaque in the vessel prior to positioning the sealing tip within the channel of the deposited sealant. The sealing tip of the present disclosure may have a limited sized step feature that is operable by contact against a distal end surface of the location device rather than against a distal end surface of an insertion sheath. The sealing tip may be completely insertable within the insertion sheath. In some arrangements, the sealing tip may be operable without a step feature intended for contact against an end surface of the insertion sheath or the end surface of a carrier tube through which the connection member extends.

Another aspect of the present disclosure relates to the angled shape of a distal end portion of the sealing tip. The sealing tip may include a distal head portion having a distal surface that is arranged at an angle relative to a longitudinal axis of the sealing tip or a longitudinal axis of the location device. The distal surface may be arranged at an angle that substantially matches an angle of insertion of the vascular closure device through a percutaneous incision that provides access to the vessel puncture. The angle may be in the range of about 30° to about 60°, and more specifically in the range of about 30° to about 50°. The angle of the distal surface may be arranged non-perpendicular to a length dimension (e.g., longitudinal axis) of the sealing tip. The angled shape of the distal surface and other features of the sealing tip may provide a lack of symmetry along a length of the sealing tip. The lack of symmetry may promote rotation of the sealing tip about an axis extending transversely through the sealing tip relative to a length dimension of the sealing tip. The rotation about a transversely arranged axis may assist in lodging the sealing tip in the channel, which is formed in the deposited sealant.

Referring now to FIGS. 1-3, an example vascular closure device 10 is shown including a sealant delivery device 12 and a balloon location device 14. The balloon location device 14 is inserted through a lumen of the sealant delivery device 12 to position a detachable sealing tip 48 distal of a distal opening 36 of a sealant delivery lumen of the sealant delivery device 12. The detachable sealing tip is positioned distal of a balloon 24 carried at least in part by one of the sealant delivery device 12 and balloon location device 14.

The sealant delivery device 12 includes a manifold 20, a delivery tube 22, and a balloon 24. The manifold 20 includes a delivery device passage 26, an injection port 28, and a connector 30. The delivery tube 22 includes a first lumen 32 and a second lumen 34. The first lumen 32 includes a distal opening 36. The balloon 24 includes distal and proximal waists 38, 40. A volume of sealant is delivered through the injection port 28 and into the first lumen 32, and is deposited adjacent to a vessel puncture upon ejection from the distal opening 36.

The distal and proximal waists 38, 40 of balloon 24 may be connected to a distal end portion of the delivery tube 22. In other arrangements, only the proximal waist 40 is connected to the distal end portion of the delivery tube 22, and the distal waist 38 is connected to a portion of the balloon location device 14. As mentioned above, the second lumen 34 may provide a path for inflation fluid to be delivered to the balloon 24. In other arrangements, the inflation fluid is delivered through the balloon location device 14.

The balloon location device 14 may include a housing or handle 42, a carrier tube 44, an inflation manifold 46, a detachable sealing tip 48, and a sealing tip connection member 50. The housing 42 is connected to a proximal end 56 of the carrier tube 44. In at least some arrangements, the distal waist 38 is connected to a distal end 54 of the carrier tube 44 (see FIG. 1B). The carrier tube 44 may include an inflation lumen 58 and a connector lumen 60. In other arrangements, the inflation lumen 58 and connector lumen 60 are integrated into a single lumen, such as when the second lumen 34 of sealant delivery device 12 provides delivery of inflation fluid to the balloon 24. The inflation lumen 58 may include a distal opening 59 arranged in flow communication with the balloon 24. The distal opening 59 may be positioned proximal of the detachable sealing tip 48 (see FIG. 3).

The inflation manifold 46 may be connected to a source of inflation fluid 7. The inflation manifold 46 may be positioned at any desired location relative to the manifold 20 of sealant delivery device 12 and housing 42. Inflation manifold 46 is typically coupled in flow communication with the inflation lumen 58.

The detachable sealing tip 48 may be mounted to the distal end 54 of carrier tube 44. A portion of the detachable sealing tip 48 may be inserted within the carrier tube 44 such as, for example, within the connector lumen 60 (see FIG. 1B).

The detachable sealing tip 48 may include a head portion 70 and a body portion 72. The head portion 70 may include a proximal step surface 74 (also referred to as a stop feature)

defined between the head and body portions 70, 72, and a distal surface 75. In other arrangements, the head portion 70 may have the same peripheral size and shape as the body portion 72 so there is no proximal step surface 74.

Figure 4:
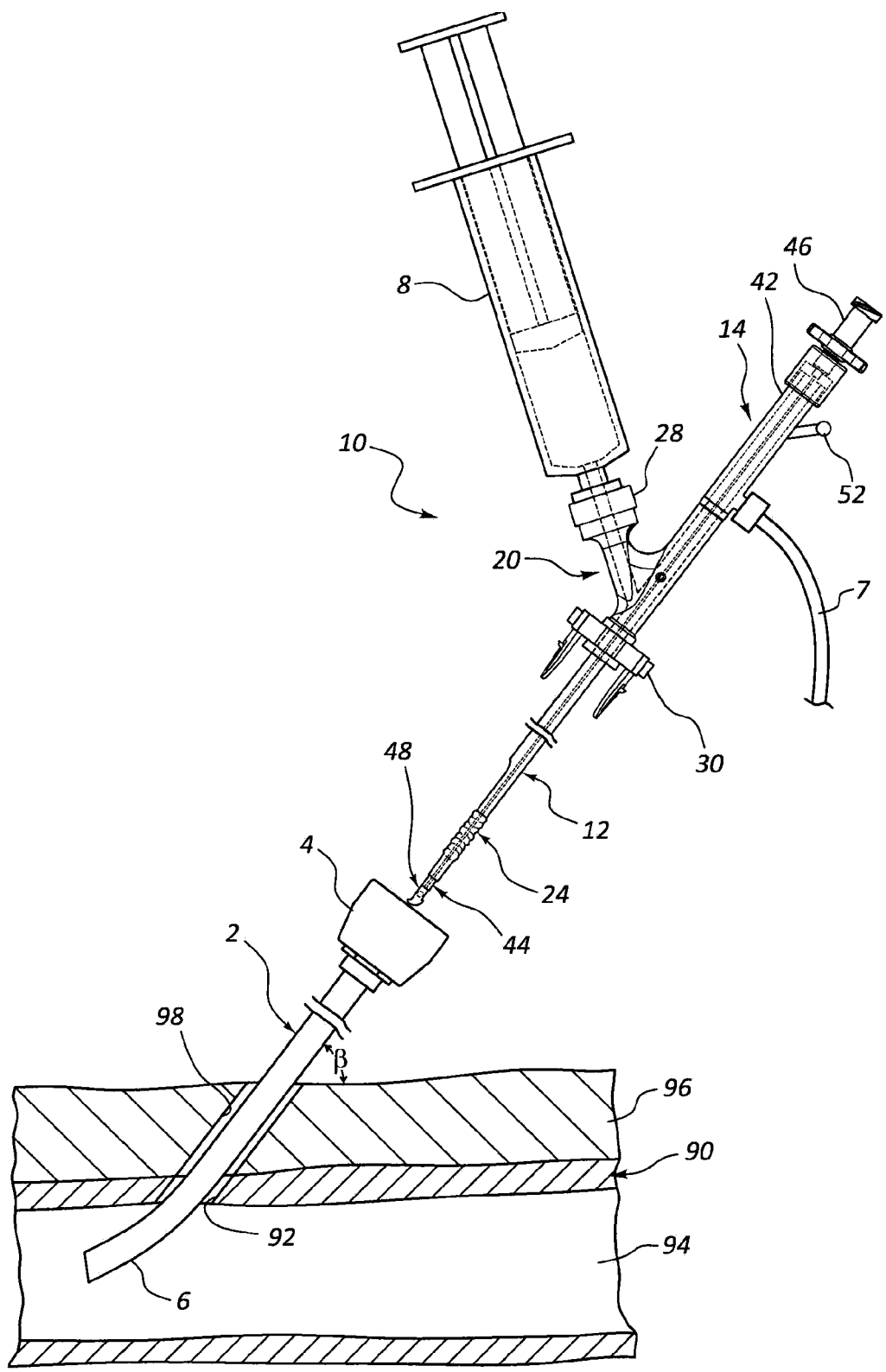
FIGS. 4-8 show steps of sealing a vessel puncture using the vascular closure device of FIG. 1.

The proximal step surface 74 may be arranged at an angle $\theta_1$ relative to a length dimension (e.g., longitudinal axis of the body portion 72). The angle $\theta_1$ is typically about the same as the angle of insertion β of the vascular closure device 10 into a patient through a percutaneous incision as shown in FIG. 4. For example, the angle $\theta_1$ may be in the range of about 30° to about 60°, and more particularly about 40° to about 50°. The angle of distal surface 75 may orient the distal surface 75 flush against an outer surface of the vessel adjacent to the vessel puncture, or within the vessel puncture and flush with an inner surface of the vessel lumen.

The distal surface 75 may have a tapered shape that provides a proximally tapered leading surface for the detachable sealing tip 48. In some arrangements, the distal surface 75 may be contoured, whereas in other arrangements the distal surface 75 has a planar or polygonal shape.

The body portion 72 may include a cavity 76, a side opening 78, a proximal opening 80, and a stop surface 82 (see FIGS. 1B and 9A-11B). The cavity 76 is accessible through the side opening 78 and the proximal opening 80. The side opening 78 may have a greater size than the proximal opening 80.

The body portion 72 may also include a plurality of expandable members 84A-D positioned at a proximal end portion thereof. The expandable members 84A-D may be arranged circumferentially around the proximal opening 80. The body portion 72 may include a plurality of radial cuts 85 extending from an outer circumferential surface of the body portion 72 to the proximal opening 80. The radial cuts 85 may define the expandable members 84A-D in the body portion 72. At least some of the expandable members 84A-D may expand radially outward as shown in FIG. 2B. Drawing the sealing tip connection member 50 through the proximal opening 80 may apply a radially outward directed force that moves the expandable members 84A-D radially outward. The expandable members 84A-D in the radially outward position shown in FIG. 2B may assist in lodging or fixing the detachable sealing tip 48 within a volume of sealant used to seal the vessel puncture.

The sealing tip connection member 50 includes distal and proximal ends 62, 64, and a connection portion 66 (also referred to as a retention member). The sealing tip connection member 50 may have an elongate structure in the form of, for example, a wire, suture, braid, or other type of filament. The connection portion 66 may have an enlarged size (e.g. maximum width or thickness dimension) as compared to a thickness or diameter of remaining portions of the sealing tip connection member 50. For example, the sealing tip connection member 50 may have a thickness $T_1$ in the range of about 0.5 mm to about 2 mm. A maximum dimension $T_2$ of the connection portion 66 may be in the range of about 2 mm to about 5 mm. In some arrangements, the dimension $T_2$ is at least two times greater than the dimension $T_1$ of the sealing tip connection member 50 (see FIG. 2B). The dimension $T_2$ is typically greater than a minimum dimension $D_1$ of the proximal opening 80. The connection portion 66 may contact the stop surface 82 adjacent to the proximal opening 80 to at least temporarily hold the connection portion 66 within the cavity 76 (see FIG. 1B) until a tension force is applied to the proximal end 64 to draw the connection portion 66 through the proximal opening 80.

The sealing tip connection member 50 may extend through a hypotube 53 (see FIG. 1B). The hypotube 53 may be positioned in the connection lumen 60. The hypotube 53 may abut against the detachable sealing tip 48, or may be spaced proximally from the detachable sealing tip 48 and within the connection lumen 60.

Referring to FIGS. 9A and 9B, the balloon location device 14 is assembled by inserting a proximal end 64 of the sealing tip connection member 50 through the side opening 78, into the cavity 76, and out through the proximal opening 80. The sealing tip connection member 50 is advanced through the cavity 76 until the connection portion 66 contacts the stop surface 82 as shown in FIGS. 10A and 10B. The proximal end 64 of the sealing tip connection member 50 is advanced through the connector lumen 60 of the carrier tube 44 to a proximal position available for actuation by an operator (e.g., using actuator 52). The body portion 72 of the detachable sealing tip 48 may be abutted against a distal end surface of the carrier tube 44 as shown in FIGS. 11A and 11B.

The sealing tip connection member 50 is disconnected from the detachable sealing tip 48 to release the detachable sealing tip 48 from the vascular closure device 10. Applying a tension force in the sealing tip connection member 50 pulls the connection portion 66 through the proximal opening 80, thereby releasing the detachable sealing tip 48. Drawing the connection portion 66 through the proximal opening 80 may move (e.g., actuate) at least one of the expandable members 84A-D into a radially expanded position to act as an anchor feature for the detachable sealing tip 48. Tension may be applied in the sealing tip connection member 50 using the actuator 52 (see FIG. 1). The sealing tip connection member 50 may be connected to the actuator 52, and operating the actuator 52 (e.g., rotating the actuator through a pivot motion) may apply tension in and proximally move the sealing tip connection member 50.

The detachable sealing tip 48 may be released from the vascular closure device 10 without using an insertion sheath (e.g., delivery sheath 2 shown in FIGS. 4-8) as a backstop. In other arrangements, the balloon location device 14 includes a separate tube (e.g. the hypotube 53 or a polymer tube) or other backstop feature positioned within the connector lumen 60. The sealing tip connection member 50 may extend through the separate tube or backstop feature. The separate tube or backstop feature may support the detachable sealing tip 48 while applying the tension force in sealing tip connection member 50 to remove the connection portion 66 through the proximal opening 80.

As mentioned above, the sealing tip connection member 50 may be detachable from the detachable sealing tip 48 using other operations such as, for example, advancing or rotating the sealing tip connection member 50 relative to the detachable sealing tip 48. Alternatively, the sealing tip connection member 50 may be severed or cut at a location near the distal end of the balloon location device 14, or at a proximal end near the housing 42. This severing or cutting of the sealing tip connection member 50 may provide temporary disconnection of the detachable sealing tip 48 from the balloon location device 14. The sealing tip connection member 50 may be trimmed at or below the skin surface of the patient upon removal of the vascular closure device 10 from the patient.

The detachable sealing tip 48 may have an outer profile that is no greater than an outer profile of the carrier tube 44 of the balloon location device 14. The detachable sealing tip 48 may have an outer profile that is no greater in size than an outer profile of any portion of the balloon location device 14 arranged distal of the housing 42. For example, a maximum dimension $D_4$ of the detachable sealing tip 48 may be no greater than a maximum dimension $D_3$ of the carrier tube 44 as shown in FIG. 9B. The detachable sealing tip 48 may be detachable from the balloon location device 14 without the use of a friction or interference fit between the detachable sealing tip 48 and the channel of the sealant within which the detachable sealing tip 48 is deposited.

Figure 5:
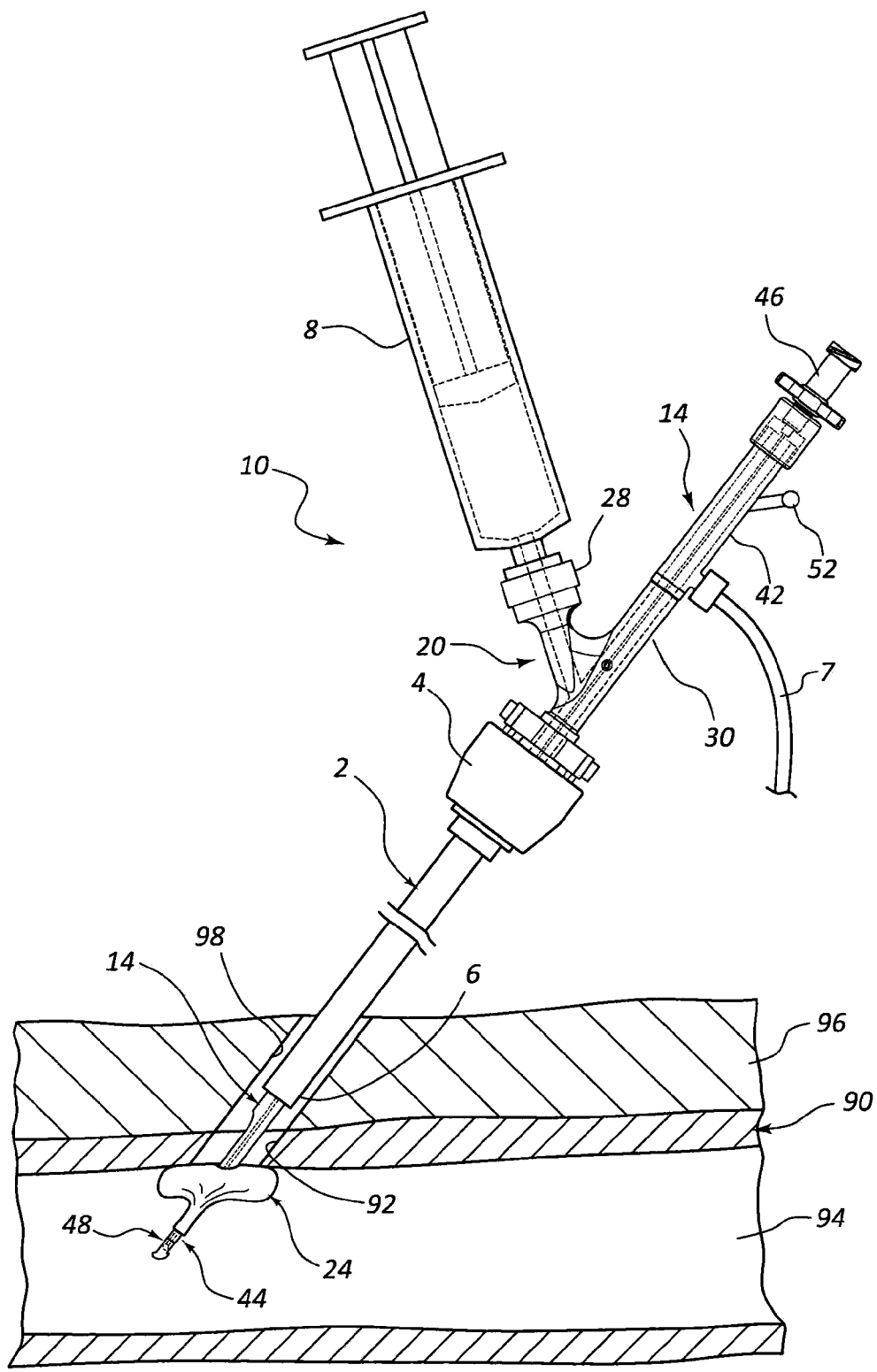

Referring now to FIGS. 4-8, the vascular closure device 10 is shown involved in operational steps of sealing a vessel puncture 92 in a vessel 90. The vessel puncture 92 is accessible through a tissue puncture 98 (also referred to as a percutaneous incision) in a tissue layer 96. Referring to FIG. 4, a delivery sheath or insertion sheath 2 is advanced through the tissue puncture 98 and through the vessel puncture 92 into a vessel lumen 94 of the vessel 90. The vascular closure device 10 may be aligned with an opening through a hub 4 of the delivery sheath 2. FIG. 5 shows the vascular closure device 10 inserted through the delivery sheath 2 until the balloon 24 and detachable sealing tip 48 are positioned distal of a distal end 6 of the delivery sheath 2. The connector 30 of sealant delivery device 12 may connect to the hub 4 of the delivery sheath 2 so that the delivery sheath 2 and vascular closure device 10 move in tandem.

A volume of inflation fluid is delivered from a source of inflation fluid 7 and through the vascular closure device 10 to fill the balloon 24 as shown in FIG. 5. The vascular closure device 10 and delivery sheath 2 are withdrawn proximally to contact the inflated balloon 24 against an inner surface of the vessel 90 adjacent to the vessel puncture 92. The balloon 24 may provide temporary sealing of the vessel puncture 92 (e.g., temporary hemostasis).

Figure 6:
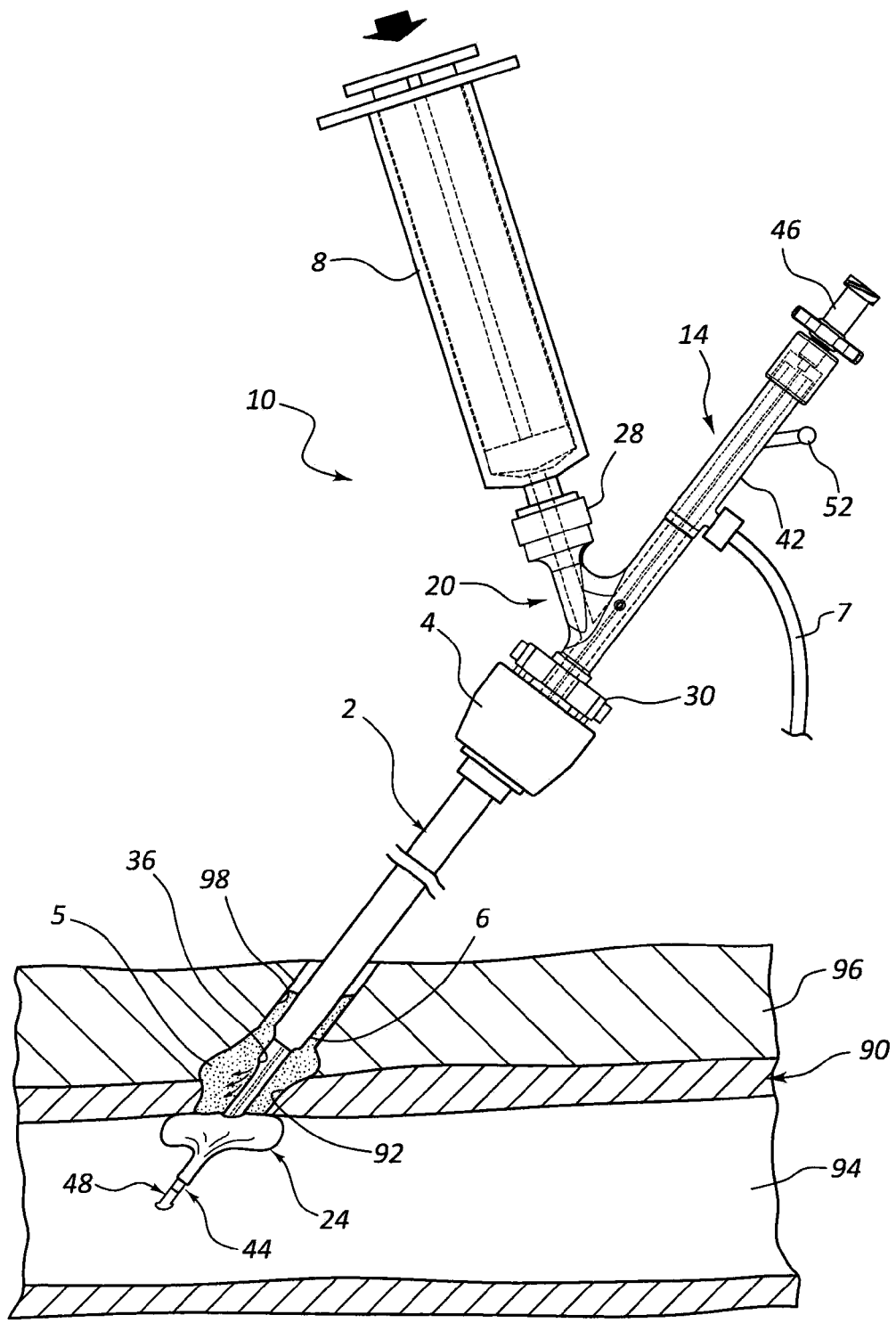

Referring to FIG. 6, a volume of sealant is delivered via a sealant source 8 through the sealant delivery device 12 and ejected through the distal opening 36 of the first lumen 32 at a location adjacent to the vessel puncture 92. The sealant forms a sealant plug 5 that fills the vessel puncture 92 and at least a portion of the tissue puncture 98. Typically, the sealant is allowed to cure to form a solid or semi-solid plug structure before deflating the balloon 24. Allowing the sealant to form into sealant plug 5 limits the risk of the sealant moving into the vessel lumen 94 after deflating the balloon 24.

Figure 7:
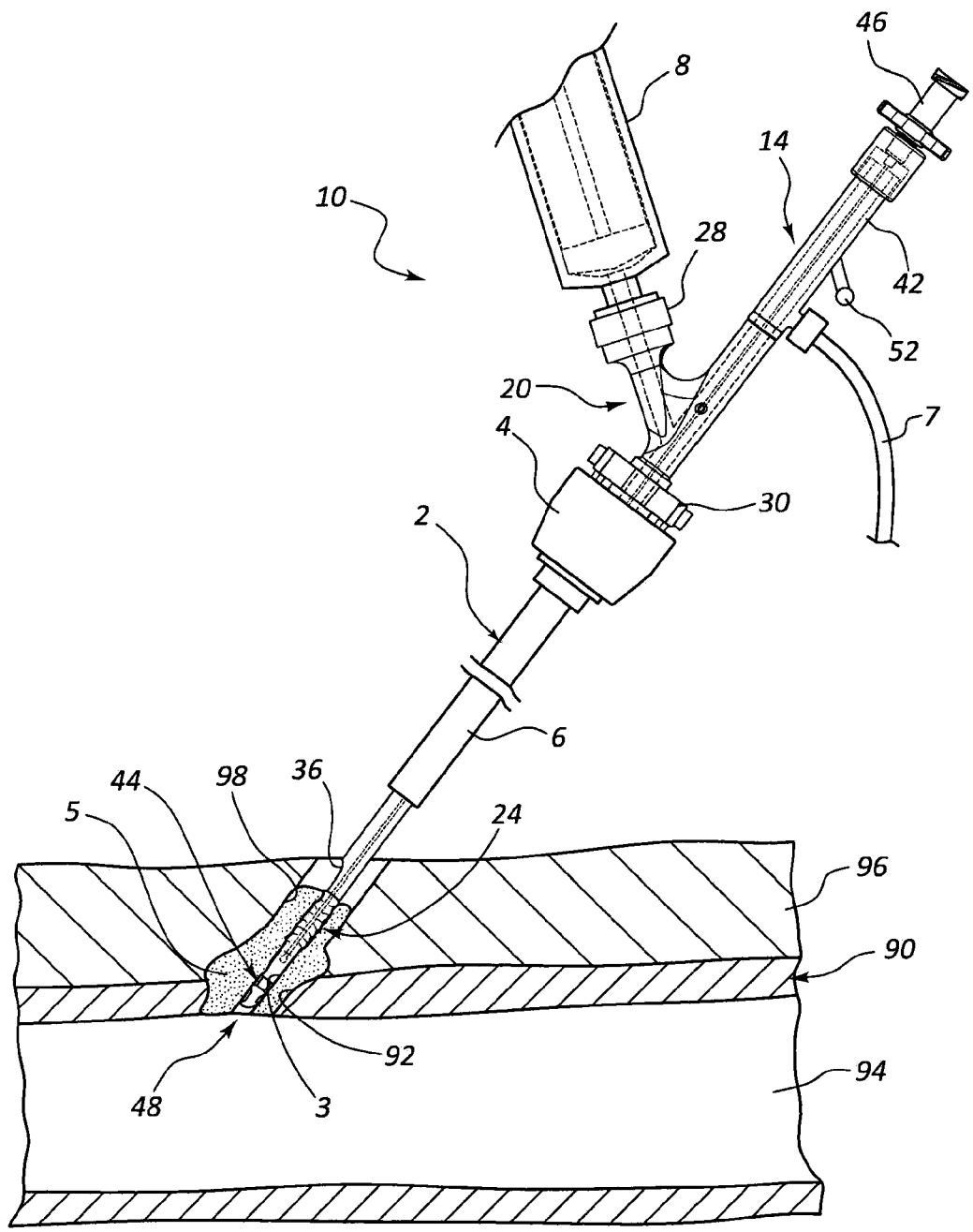

FIG. 7 shows the balloon 24 deflated and the vascular closure device 10 withdrawn through the sealant plug 5. Removal of the vascular closure device 10 forms a channel 3 through the sealant plug 5. The vascular closure device 10 is withdrawn to a position in which the detachable sealing tip 48 is positioned within the channel 3. The operator may then operate the actuator 52 to release the detachable sealing tip 48 from the balloon location device 14 to seal the channel 3. As discussed above, the detachable sealing tip 48 may be released by disconnecting the sealing tip connection member 50 from the detachable sealing tip 48.

The angled shape of the distal surface 75 may align with an interior or exterior surface of the vessel 90. The angled shape of the distal surface 75 may provide a flush mount arrangement of the detachable sealing tip 48 with the interior or exterior surface of the vessel 90. The angle shape of the distal surface 75 may help maintain the detachable sealing tip 48 outside of the vessel lumen 94 while the detachable sealing tip 48 is positioned as close to the vessel interior as possible (see FIG. 8).

Figure 8:
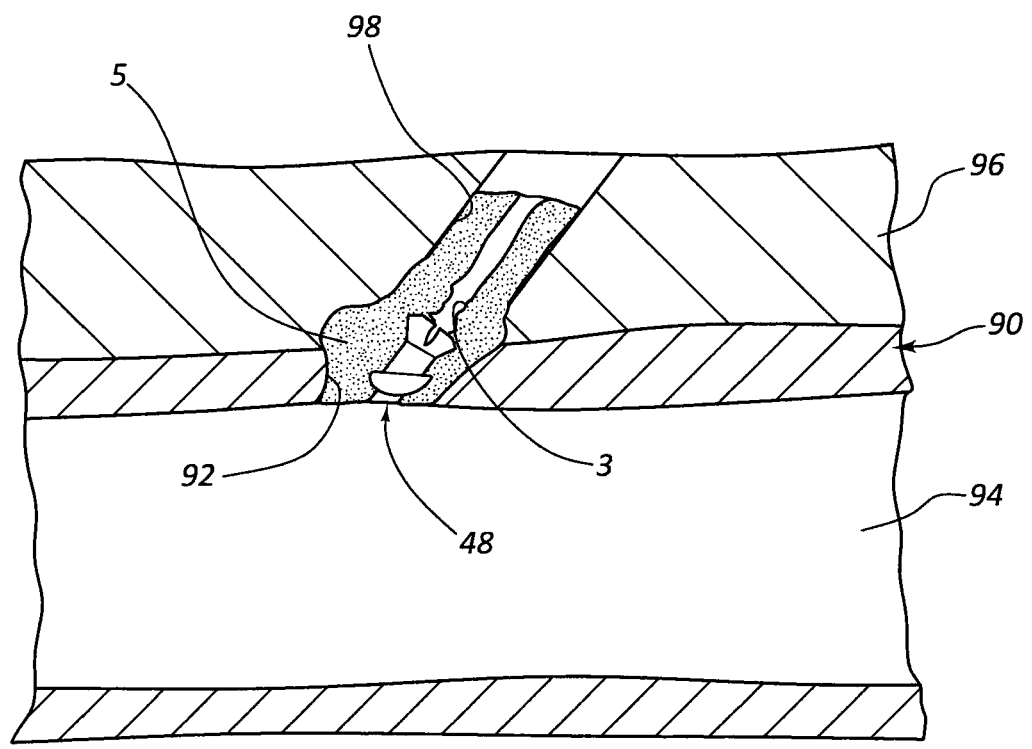

After detaching the detachable sealing tip 48, the vascular closure device 10 may be completely removed from the patient to leave behind the sealant plug 5 with the channel 3 at least partially filled (e.g., plugged or sealed) by the detachable sealing tip 48 (see FIG. 8). The detachable sealing tip 48 may be positioned at any location along the length of the channel 3. The detachable sealing tip 48 may be positioned spaced apart from the vessel lumen 94. The detachable sealing tip may be positioned outside of the vessel wall such as adjacent to an exterior wall of the vessel 90.

Figure 12:
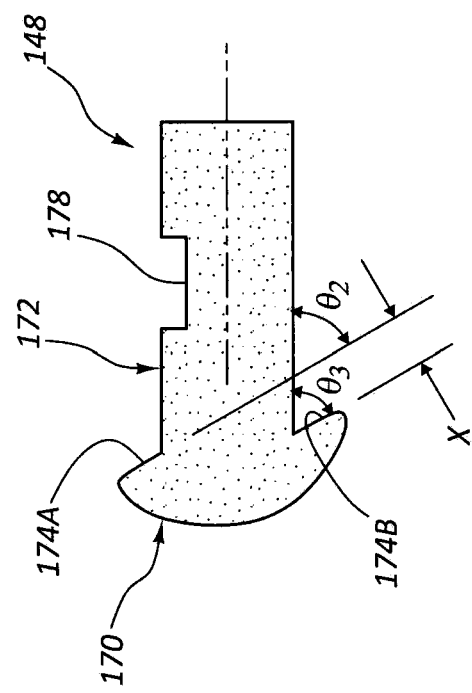
FIG. 12 is a side view of another example detachable sealing tip for use in the vascular closure devices disclosed herein.

Referring now to FIGS. 12-15F, several additional detachable sealing tip embodiments are shown and described. FIG. 12 shows a detachable sealing tip 148 having a head portion 170 and a body portion 172. The detachable sealing tip 148 may include first and second step surfaces 174A, 174B. The first step surface 174A may be arranged at an angle $\theta_2$ relative to a length dimension (e.g., longitudinal axis) of the detachable sealing tip 148. The second step surface 174B may be arranged at a separate angle $\theta_3$. The angles $\theta_2$ and $\theta_3$ may be the same. Alternatively, the angles $\theta_2$ and $\theta_3$ may be different from each other. The first and second step surfaces 174A, 174B may be spaced apart a distance X as shown in FIG. 12. The offset nature of the first and second step surfaces 174A, 174B may position the step surfaces at substantially the same axial position along a length of the detachable sealing tip 148. The offset arrangement of the first and second step surfaces 174A, 174B may promote improved fixing or lodging of the head portion 170 within the channel 3 in the deposited sealant.

The head portion 170 may have any desired shape and size. In at least one example, a distal surface of the detachable sealing tip 148 defined by the head portion 170 may have a contoured shape. In other examples, the distal surface may have a tapered shape (e.g., tapered in a proximal direction) and may be planar.

Figure 13:
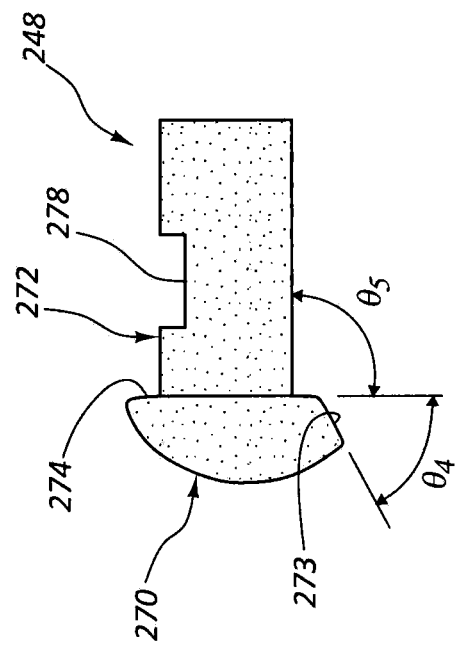
FIG. 13 is a side view of another example detachable sealing tip for use in the vascular closure devices disclosed herein.

Referring to FIG. 13, another example detachable sealing tip 248 is shown including a head portion 270 and a body portion 272. The head portion 270 may include a catch surface 273 positioned at a peripheral edge of the head portion 270 adjacent to a step surface 274. The catch surface 273 may be arranged at an angle $\theta_4$ relative to the step surface 274. The step surface 274 may be arranged at an angle $\theta_5$ relative to a length dimension (e.g., longitudinal axis) of the detachable sealing tip 248. The catch surface 273 may assist in fixing or lodging the detachable sealing tip 248 within a channel 3 formed through a deposited volume of sealant. The catch surface 273 may promote rotation of the detachable sealing tip 248 about an axis extending laterally through the detachable sealing tip 248 (e.g., perpendicular to a length dimension or longitudinal axis of the detachable sealing tip 248). The detachable sealing tip 248 may include a plurality of catch surfaces 273 spaced around a circumference of the head portion 270. The catch surfaces 273 may be arranged at the same or different angles $\theta_4$ relative to the step surface 274.

In at least one example, the angle $\theta_5$ of the step surface 274 may be arranged at a 90° angle relative to a length dimension of the detachable sealing tip 248. In other examples, the angle $\theta_5$ may be in a range of about 45° to about 135°, and more particularly in the range of about 80° to about 100°. The angle $\theta_4$ may be in the range of about 90 degrees, and more particularly in the range of about 30° to about 60°.

The detachable sealing tips 148, 248 may include a side opening 178, 278, respectively, for inserting a sealing tip connection member through a portion of the detachable sealing tips 148, 248. The detachable sealing tips 148, 248 may include the expandable members described above with reference to the detachable sealing tip 48.

Referring to FIGS. 14A-14D, another example detachable sealing tip 348 is shown including a head portion 370 and a body portion 372. The head portion 370 includes a distal surface 375. A proximal step surface 374 may be formed between the head portion 370 and body portion 372. The body portion 372 includes a cavity 376 (see FIG. 14A), a side opening 378, and a proximal opening 380. At least one alignment member 386 may be positioned along an exterior of the body portion 372. The alignment members 386 may be aligned with a longitudinal axis along a length dimension of the detachable sealing tip 348. The alignment members 386 may extend proximally from the head portion 370 and along the body portion 372. The alignment members 386 may contact the proximal step surface 374. The alignment members 386 may include a pair of alignment members 386 positioned at circumferentially spaced apart locations. The pair of alignment members 386 may be arranged coplanar, as shown in FIG. 14D. Other arrangements are possible in which only a single alignment member 386 is provided or three or more alignment members 386 are provided at locations around an outer periphery of the body portion 372.

The alignment members 386 may assist in limiting rotational movement of the detachable sealing tip 348 about a longitudinal axis of the detachable sealing tip 348 (e.g., an axis extending coaxially with the proximal opening 380). The alignment members 386 may contact an internal surface of the channel 3 formed in the deposited sealant within which the detachable sealing tip 348 is positioned.

The alignment members 386 may permit at least some rotation about various rotation axes $R_1$, $R_2$ (see FIG. 14B) after the detachable sealing tip 348 is detached from the balloon location device 14. The rotation axes $R_1$, $R_2$ may extend laterally through the detachable sealing tip 348 in a direction perpendicular to a longitudinal axis extending along a length of the detachable sealing tip 348. The rotation axis $R_1$ may represent rotation in a counterclockwise direction, and rotation axis $R_2$ may represent rotation in a clockwise direction. Rotation about one of the rotation axes $R_1$, $R_2$, or other rotation axis extending laterally through the detachable sealing tip 348 at any position along a length or around an outer peripheral surface of the detachable sealing tip 348 may provide increased lodging or fixing of the detachable sealing tip 348 within the channel 3. The head portion 370 and the proximal step surface 374 may contact the internal surface of the channel 3 to fix or lodge the detachable sealing tip 348 within the channel 3. In at least some examples, the rotation axes $R_1$, $R_2$ are arranged coplanar with the alignment members 386.

The detachable sealing tip 348 may include a side opening 378 through which a portion of the sealing tip connection member 50 extends as part of assembling the detachable sealing tip 348 with a balloon location device. The proximal step surface 374 may be arranged at an angle $\theta_1$ similar to the construction of the detachable sealing tip 48 described above with reference to FIGS. 1-1B.

The alignment members 386 may be positioned at other locations along the detachable sealing tip 348. In one example, at least one of the alignment members 386 is positioned proximal of the side opening 378. In other arrangements, at least a portion of at least one of the alignment members 386 is positioned on or extends from a portion of the head portion 370. The alignment members 386 may extend along an entire length of the detachable sealing tip 348. In some examples, at least one of the alignment members 386 extends along an entire length of the body portion 372 (e.g., from the proximal step surface 374 to a proximal most end of the body portion 372). A greater length for the alignment members 386 may limit rotation about the rotation axes $R_1$, $R_2$.

Figure 15D:
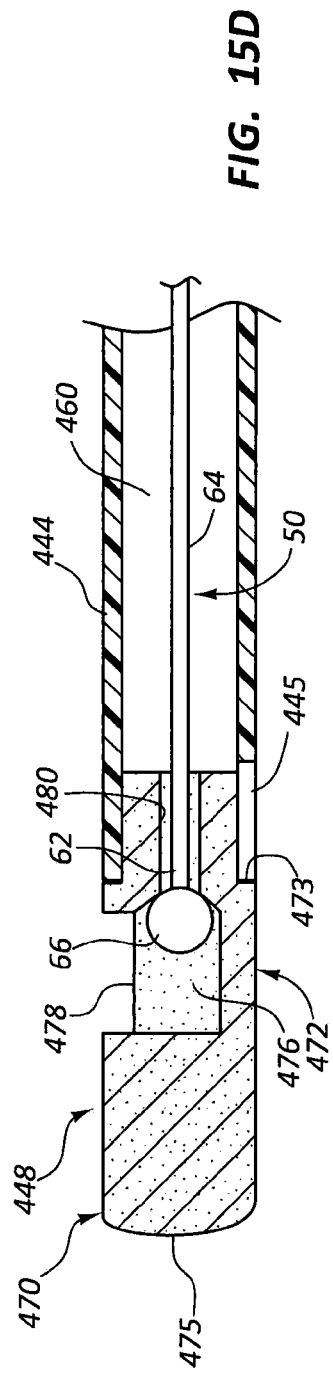

Referring now to FIGS. 15A-15F, another example detachable sealing tip 448 is shown including a head portion 470 and a body portion 472. The detachable sealing tip 448 may have an improved connection to a carrier tube 444 during delivery of the detachable sealing tip to the channel 3. A portion of the detachable sealing tip 448 may extend into the carrier tube 444 when assembled, as shown in FIG. 15D.

The head portion 470 may include a distal surface 475 (see FIG. 15C). A step 473 is formed at the body portion 472 at a location proximal of a side opening 478. The step 473 may provide a reduced diameter portion at a proximal end of the body portion 472 that is sized to be inserted into a connector lumen 460 of the carrier tube 444 as shown in FIG. 15D. A distal end surface of the carrier tube 444 may abut against the step 473.

The side opening 478 leads to a cavity 476. A proximal opening 480 intersects with the cavity 476. The sealing tip connection member 50 is insertable through the side opening 478 and proximal opening 480, and the connection portion 66 is lodged within the cavity 476 as shown in FIGS. 15C-15D. After the connection portion 66 is positioned within the cavity 476 as shown in FIG. 15C, the proximal end of the body portion 472 may be inserted into the carrier tube 444 as shown in FIG. 15D.

Figure 15E:
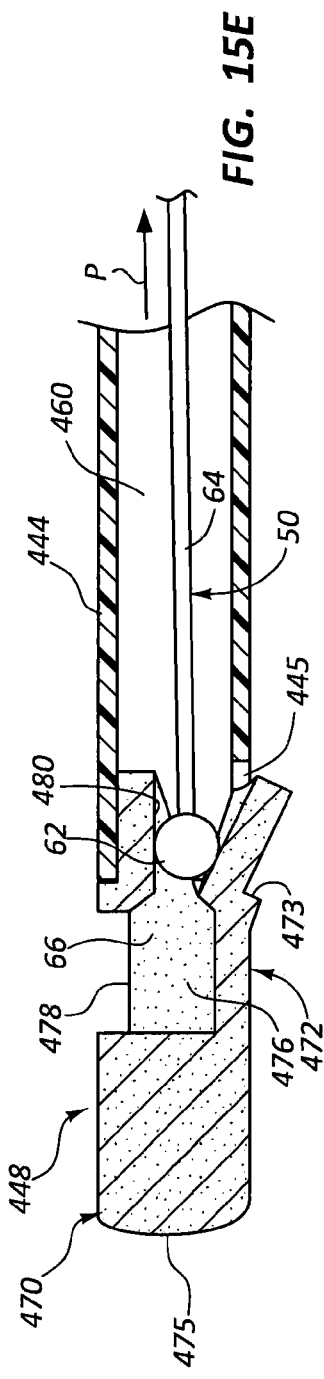

Applying a tension force in the sealing tip connection member 50 in a proximal direction P as shown in FIG. 15E pulls the connection portion 66 through the proximal opening 480 as shown in FIG. 15E. The connection portion 66 applies a radially outward directed force that moves an expandable member 484 of the detachable sealing tip 448 in a radially outward direction. The expandable member 484 may be defined at least in part by a pair of cuts 485 (see FIGS. 15A and 15B), which extend from an exterior surface of the body portion 472 to the proximal opening 480. The carrier tube 444 may include a cutout portion 445 as shown in FIGS. 15B-15E. The expandable member 484 may extend radially outward through the cutout portion 445 as the connector portion 66 passes through the proximal opening 480.

Figure 15F:
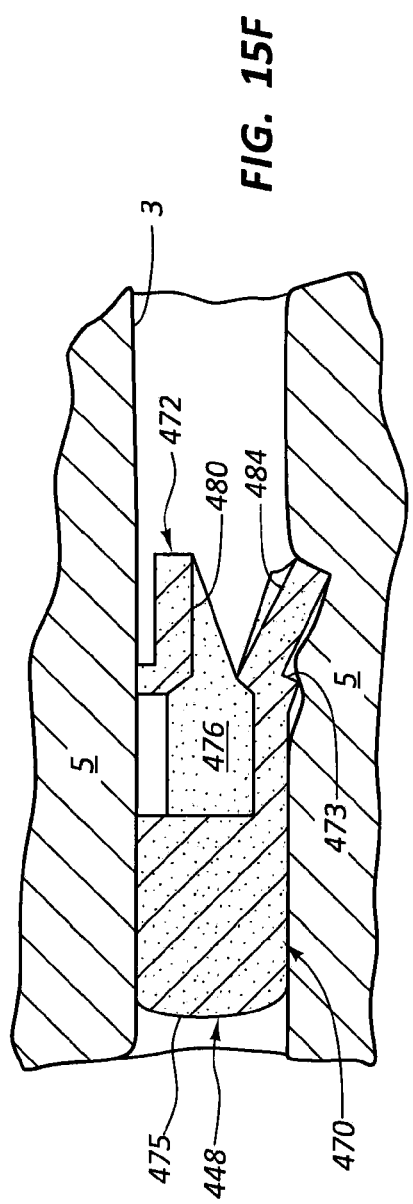

Removing the sealing tip connection member 50 from the detachable sealing tip 448 permits the detachable sealing tip 448 to be disconnected from the carrier tube 444. The detachable sealing tip 448 may be left behind in a channel 3 of a sealant plug 5 as shown in FIG. 15F. The expandable member 484 in a radially expanded position as shown in FIG. 15F may assist in fixing or lodging the detachable sealing tip 448 within the channel 3. The expandable member 484 may limit axial movement of the detachable sealing tip 448 within the channel 3.

The detachable sealing tip 448 may include a tapered distal surface 475 such as is included in at least one of the detachable sealing tips 48, 148, 248 described above. Further, the detachable sealing tip 448 may include a proximal step surface positioned at a location distal of the side opening 478 and between the head portion 470 and body portion 472.

The expandable members described above (e.g., expandable members 84A-D and 484) may undergo plastic deformation as part of moving from the initial rest state into a radially expanded position (e.g., see FIGS. 2B and 15F). The plastic deformation may provide a fixed position for the expandable member in the radially expanded position. Accordingly, the expandable members described herein may act as an anchor for securing the detachable sealing tip within a channel of a sealant plug deposited as part of sealing a vessel puncture (e.g., as described above with reference to FIGS. 4-8).

Any of the features described herein with reference to the detachable sealing tips 48, 148, 248, 348, 448 may be interchangeable with each other to provide functionality useful for various applications of a detachable sealing tip. For example, any of the detachable sealing tip configurations disclosed herein may be modified to be at least partially insertable into an open distal end of a carrier tube or an insertion sheet. The detachable sealing tip may include an expandable feature that expands radially outward through a side wall of the carrier tube or insertion sheath to which the detachable sealing tip is mounted or is at least partially inserted into during delivery of the detachable sealing tip to a vessel puncture. An example detachable sealing tip may include expandable members, alignment features, features that promote rotation about an axis extending laterally through the detachable sealing tip, or features that limit rotation about a longitudinal axis of the detachable sealing tip. The detachable sealing tip may be configured to intentionally rotate about a lateral axis passing through the detachable sealing tip to assist in lodging the detachable sealing tip within a channel formed in a sealant plug. The rotation may occur as part of disconnecting the detachable sealing tip from the device carrying the detachable sealing tip, or after being detached.

Other aspects of the present disclosure are related to methods of assembling a vascular closure device that includes a detachable sealing tip. Other methods are directed to sealing a vessel puncture using a vascular closure device having a detachable sealing tip.

One aspect of the present disclosure is directed to a device (e.g., detachable sealing tip) used to seal an opening left in a volume of tissue adhesive (e.g., sealant) deposited using a location/sealing device for an extravascular closure application. The detachable sealing tip is designed so that after it has been deployed, rotation of the detachable sealing tip about any Y-axis, Z-axis, or other axis extending perpendicular to a longitudinal X-axis of the sealing tip will lock the detachable sealing tip in place inside the tract left behind by removal of the device through the tissue adhesive. Typically, any cylindrical shaped design for the detachable sealing tip has the potential to be easily pushed distally out of the tract left in the tissue adhesive because there is no feature to hold the detachable sealing tip in place. The actuation of releasing the detachable sealing tip may be used to create rotation of the detachable sealing tip and lock the detachable sealing tip in place inside of the tract.

Another aspect of the present disclosure relates to the operation of releasing the detachable sealing tip causing a conformational change in the shape of the sealing tip. For example, releasing the detachable sealing tip may create radial expansion of portions of the sealing tip. In other examples, releasing the detachable sealing tip may create expansion in a single direction, or otherwise move the detachable sealing tip so that the detachable sealing tip locks in place in the tract through the tissue adhesive.

Generally, the systems, devices and methods described herein may create active locking of a detachable sealing tip within a deposited bioadhesive (e.g., tissue adhesive or sealant) used to seal a vessel puncture extravascularly. Actively securing the detachable sealing tip in a specific axial direction may limit movement of the detachable sealing tip in a undesirable distal direction, which may lead to positioning of all or portions of the detachable sealing tip within a vessel being plugged with the bioadhesive.

The sealants discussed herein may comprise a single component, or may comprise multiple sealant components that are mixed together. The multiple sealant components may further react together to form a cross-linked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical cross-linking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention.

What is claimed is:

1. A vascular closure device, comprising:
a carrier tube having a distal end;
a sealing tip releasably connected to the distal end of the carrier tube;
a sealing tip connection member extending through the sealing tip and having a proximal portion extending proximally from the sealing tip;
wherein applying a tension force at the proximal portion of the sealing tip connection member removes the sealing tip connection member from the sealing tip, and removing the sealing tip connection member from the sealing tip radially expands a portion of the sealing tip.

2. A vascular closure device according to claim 1, wherein the sealing tip connection member comprises a wire having a retention member at a distal end thereof, and applying a tension force in the wire pulls the retention member through the sealing tip.

3. A vascular closure device according to claim 1, wherein the sealing tip includes a body portion and a head portion, the body portion having a proximal passage through which the sealing tip connection member passes.

4. A vascular closure device according to claim 3, wherein the head portion includes a distal end surface arranged at a non-perpendicular angle relative to a longitudinal dimension of the body portion.

5. A vascular closure device according to claim 1, wherein the carrier tube includes a lumen, and the sealing tip connection member extends through the lumen.

6. A vascular closure device according to claim 5, further comprising a hypotube extending through the lumen, and the sealing tip connection member extends through the hypotube.

7. A vascular closure device according to claim 2, wherein the sealing tip includes a cavity sized to receive the retention member of the sealing tip connection member, the retention member exerting a radially outward directed force to the sealing tip as the sealing tip connection member is removed from the sealing tip.

8. A vascular closure device according to claim 7, wherein the cavity is accessible from a first opening in a sidewall of the sealing tip and a second opening in a proximal end portion of the sealing tip, the sealing tip connection member being insertable through the first opening and out of the second opening with the retention member being retained in the cavity.

9. A vascular closure device according to claim 1, wherein the sealing tip includes a plurality of radially expandable arms positioned at a proximal end of the sealing tip.

10. A vascular closure device according to claim 9, wherein the plurality of radially expandable arms are arranged circumferentially about a proximal passage of the sealing tip, and removing the sealing tip connection member from the sealing tip includes passing the sealing tip connection member through the proximal passage to radially expand the plurality of radially expandable arms.

11. A vascular closure device for sealing a vessel puncture of a patient, comprising:
 a sealant delivery device configured to deposit a volume of flowable sealant adjacent to a vessel puncture;
 a detachable sealing tip assembly configured to seal a channel formed in the volume of flowable sealant upon removal of the vascular closure device from the patient, the detachable sealing tip assembly comprising:
 a carrier tube;
 a sealing tip positioned at a distal end of the carrier tube;
 a filament having a proximal end and a distal end releasably connected to the sealing tip;
 wherein applying a tension force at the proximal end radially expands a portion of the sealing tip to lodge the sealing tip within the channel.

12. A vascular closure device according to claim 11, wherein the sealant delivery device comprises a lumen sized to receive the carrier tube.

13. A vascular closure device according to claim 11, wherein the sealing tip comprises a proximal portion having a plurality of expandable arms that expand radially upon disconnecting the filament from the sealing tip.

14. A vascular closure device according to claim 11, wherein the filament includes a connection portion at the distal end, the connection portion being positioned within the sealing tip, and disconnecting the filament from the sealing tip radially expands a portion of the sealing tip.

15. A vascular closure device according to claim 11, wherein the sealing tip includes a head portion at the distal end, the head portion having a tapered construction.

16. A method of sealing a vessel puncture, comprising:
 providing a vascular closure device having a carrier tube, a sealing tip releasably mounted to the carrier tube, and a sealing tip connection member, the sealing tip connection member extending proximally from the sealing tip;
 advancing the vascular closure device to the vessel puncture;
 delivering a volume of flowable sealant to the vessel puncture;
 withdrawing a portion of the vascular closure device through the volume of flowable sealant to form a channel in the volume of flowable sealant;
 positioning the sealing tip in the channel;
 expanding the sealing tip with the sealing tip connection member;
 disconnecting the sealing tip connection member from the sealing tip to deposit the sealing tip in the channel.

17. A method according to claim 16, wherein disconnecting the sealing tip connection member from the sealing tip includes removing a connection portion of the sealing tip connection member from within the sealing tip.

18. A method according to claim 17, wherein removing the connection portion from within the sealing tip radially expands a portion of the sealing tip.

19. A method according to claim 16, wherein disconnecting the sealing tip connection member from the sealing tip disconnects the sealing tip from the carrier tube.

20. A method according to claim 16, wherein the sealing tip includes at least one radially expandable arm, and expanding the sealing tip includes moving the at least one radially expandable arm into an expanded position.

21. A method according to claim 16, further comprising providing a sealant delivery device to deliver the volume of flowable sealant to the vessel puncture, the vascular closure device extending through the sealant delivery device.

22. A method of sealing a vessel puncture, comprising:
 providing a vascular closure device having a sealing tip and a sealing tip connection member, the sealing tip connection member extending through a portion of the sealing tip;
 advancing the vascular closure device to the vessel puncture;
 depositing a flowable sealant adjacent to the vessel puncture;
 withdrawing a portion of the vascular closure device through the deposited flowable sealant to form a channel therein;
 positioning the sealing tip in the channel;
 disconnecting the sealing tip connection member from the sealing tip to deposit the sealing tip in the channel;
 rotating the sealing tip within the channel to fix an axial position of the sealing tip in the channel.

23. A method according to claim 22, wherein rotating the sealing tip includes rotating about an axis arranged perpendicular to a length dimension of the sealing tip.

24. A method according to claim 22, wherein the sealing tip includes a head portion, a body portion, and a step feature defined between the head portion and the body portion, the method including contacting the step feature with a surface of the channel when the sealing tip rotates within the channel.

* * * * *